United States Patent
Zalit et al.

(10) Patent No.: US 11,147,766 B2
(45) Date of Patent: Oct. 19, 2021

(54) GASTRIC RETENTIVE DEVICES

(71) Applicant: CLEXIO BIOSCIENCES LTD., Jerusalem (IL)

(72) Inventors: Ilan Zalit, Rosh Ha'ayin (IL); Avshalom Ben Menachem, Zur Izhak (IL)

(73) Assignee: Clexio Biosciences Ltd., Jerusalem (IL)

( * ) Notice: Subject to any disclaimer, the term of this patent is extended or adjusted under 35 U.S.C. 154(b) by 467 days.

(21) Appl. No.: 15/780,420

(22) PCT Filed: Dec. 1, 2016

(86) PCT No.: PCT/US2016/064439
§ 371 (c)(1),
(2) Date: Jun. 14, 2018

(87) PCT Pub. No.: WO2017/096054
PCT Pub. Date: Jun. 8, 2017

(65) Prior Publication Data
US 2018/0369138 A1  Dec. 27, 2018

Related U.S. Application Data

(60) Provisional application No. 62/261,752, filed on Dec. 1, 2015.

(51) Int. Cl.
*A61K 9/00* (2006.01)
*A61M 31/00* (2006.01)
(Continued)

(52) U.S. Cl.
CPC .......... *A61K 9/0065* (2013.01); *A61K 9/4833* (2013.01); *A61K 9/4858* (2013.01);
(Continued)

(58) Field of Classification Search
CPC .. A61K 9/0065; A61K 9/0053; A61K 9/4833; A61K 9/4891; A61M 31/002; A61M 2210/1053; A61F 5/0036
See application file for complete search history.

(56) References Cited

U.S. PATENT DOCUMENTS 3,844,285 A  10/1974  Laby
4,735,804 A   4/1988  Caldwell et al.
(Continued)

FOREIGN PATENT DOCUMENTS

EP  1915990      4/2008
EP  2329810 A1   6/2011
(Continued)

*Primary Examiner* — Nathan R Price
*Assistant Examiner* — Tasnim Mehjabin Ahmed
(74) *Attorney, Agent, or Firm* — BakerHostetler

(57) ABSTRACT

Provided are devices that are configured for gastric retention for a period of at least six hours (or at least three hours if the subject is in the fasted state) while maintaining their structural integrity and releasing or holding an active or diagnostic agent into or in gastric fluid of a human subject over that period, as well as methods of delivering an agent over an extended period by orally administering such devices to a subject, uses of an enteric polymer in the formation of devices that deliver an agent over an extended period of time, and methods of making such devices.

20 Claims, 8 Drawing Sheets

(51) Int. Cl.
    *A61K 9/48*     (2006.01)
    *A61K 47/38*    (2006.01)
    *A61K 47/14*    (2017.01)
    *A61K 47/34*    (2017.01)
    *B29C 45/00*    (2006.01)
    *B29K 1/00*     (2006.01)
    *B29K 105/00*   (2006.01)

(52) U.S. Cl.
    CPC .......... *A61K 9/4866* (2013.01); *A61K 9/4891* (2013.01); *A61K 47/14* (2013.01); *A61K 47/34* (2013.01); *A61K 47/38* (2013.01); *A61M 31/002* (2013.01); *B29C 45/0001* (2013.01); *A61M 2207/00* (2013.01); *A61M 2210/1053* (2013.01); *B29K 2001/08* (2013.01); *B29K 2105/0035* (2013.01); *B29K 2105/0038* (2013.01); *B29K 2105/0094* (2013.01)

(56) References Cited

U.S. PATENT DOCUMENTS

| | | | |
|---|---|---|---|
| 4,767,627 A | 8/1988 | Caldwell et al. | |
| 5,002,772 A * | 3/1991 | Curatolo | A61M 31/002 424/438 |
| 6,685,962 B2 * | 2/2004 | Friedman | A61P 3/02 424/457 |
| 8,298,574 B2 | 10/2012 | Tsabari et al. | |
| 10,195,143 B2 * | 2/2019 | Zalit | A61K 9/0065 |
| 10,485,758 B2 * | 11/2019 | Menachem | A61K 9/0065 |
| 10,737,079 B2 * | 8/2020 | Ben Menachem | A61M 31/002 |
| 2008/0241238 A1 * | 10/2008 | Dharmadhikari | A61K 31/192 424/465 |
| 2011/0066175 A1 * | 3/2011 | Gross | A61M 25/04 606/191 |
| 2017/0106099 A1 * | 4/2017 | Bellinger | C08G 83/006 |

FOREIGN PATENT DOCUMENTS

| | | |
|---|---|---|
| JP | 2012-500230 A | 1/2012 |
| WO | 2007/010847 A1 | 1/2007 |
| WO | WO 2007/072495 | 3/2007 |
| WO | 2015/187746 A1 | 12/2015 |

\* cited by examiner

GASTRIC RETENTIVE DEVICES

CROSS-REFERENCE TO RELATED APPLICATIONS

This application is the National Stage Application of International Patent Application No. PCT/US2016/064439, filed Dec. 1, 2016, which claims the benefit of priority to U.S. Provisional Application No. 62/261,752, filed Dec. 1, 2015, the entire contents of both of which are incorporated herein by reference.

TECHNICAL FIELD

The present disclosure relates to devices that are retained within a human subject's stomach following oral administration in order to release an active or diagnostic agent over time.

BACKGROUND

Structures residing in the stomach for extended periods of time have a variety of clinical application including gastric retentive dosage forms. These systems and dosage forms are particularly useful for the delivery of drugs that:

(1) have a "narrow absorption window" in the gastrointestinal tract, for example, drugs that are preferentially absorbed in the duodenum and/or jejunum over the ileum and/or colon, or have better solubility in upper sections of the gastrointestinal (GI) tract;

(2) are intended for local treatment of proximal sections of the gastrointestinal tract (stomach and/or duodenum); and/or (3) degrade in the colon or in the intestines, etc.

Gastric retentive drug delivery systems or dosage forms have focused research in three areas of technology: namely, floating systems; systems with expanding geometry through swelling or unfolding; and bioadhesive systems.

The general concept of the expandable gastroretentive systems and dosage forms is that the system or dosage form starts in a condition or configuration suitable for swallowing. The system or dosage form then expands in the stomach to prevent gastric emptying. Eventually, the system or dosage form reduces in size to pass through the pylorus or disintegrates. Some of the original formulations with this approach are known from the veterinary world. For example, U.S. Pat. No. 3,844,285 discloses the concept of a pill that can be swallowed with wings taped down that eventually expand once water-degradable tape disintegrates. Such veterinary gastroretentive devices and formulations are sold under the tradenames Captec® and Ivomec® SR Bolus. In the area of commercialized animal products, Paratect Flex® bolus is a trilaminate sheet with a central polymeric matrix and drug load which is rolled up and held by a piece of water-soluble adhesive tape in the form of a cylindrical pill.

With respect to human oral administration, U.S. Pat. No. 5,002,772 discloses a device with a plurality of compressible retention arms attached to a controlled release device which, in the expanded configuration, resists gastrointestinal transit. U.S. Pat. Nos. 4,735,804 and 4,767,627 disclose a series of substantially planar geometric shapes, e.g., a tetrahedron formed of a bioerodible polymer that may be compressed and collapsed for oral administration. U.S. Pat. No. 8,298,574 discloses an "accordion pill", formed from a sheet with an unfolded length of more than 20 mm that is encapsulated for oral administration.

There have been many challenges in designing gastric retentive dosage forms relating to ability to scale up/manufacture/assemble, drug loading capacity, retention during fasted state, providing a desired drug release profile, ensuring structural and geometric integrity of the forms in situ, controlling intestinal degradation timing, safe transitioning and exit through the GI tract and other issues.

Gastrointestinal non-degradable devices may pose potential safety concerns while exiting while gastrointestinal biodegradable devices were unsuccessful in showing gastric retention under extreme conditions of the stomach over time. Despite the broad and increasing clinical utility of these structures, there remains a need for a device capable of withstanding gastric and intestinal conditions in for extended periods of time while providing a safe exit through the human GI tract.

SUMMARY

In one aspect the present disclosure provides a device configured for delivery of an active or diagnostic agent to a subject's gastric environment via oral administration, the device comprising a material that comprises a first enteric polymer and a pH insensitive polymer, the material maintaining structural integrity and dimensional integrity in the gastric environment and degradability in the intestinal environment of the subject.

In some embodiments, the material forms a carrier portion of the device and wherein the agent is positioned within the carrier portion.

In another aspect, the present disclosure provides gastroretentive devices that are configured for delivery of an active or diagnostic agent to a subject's gastric environment via oral administration, the device comprising a carrier portion for holding the agent, the carrier portion comprising a material that comprises a first enteric polymer and a pH insensitive polymer, the material maintaining structural integrity and dimensional integrity in the gastric environment and degradability in the intestinal environment of the subject.

In some embodiments of the devices, the device is retained in the gastric environment for a period of time sufficient for release of the agent into the gastric environment. Such time period may be at least six hours or at least 8 hours or at least 10 hours or at least 12 hours or at least 18 hours or at least 24 hours or at least 48 hours or at least 72 hours. In some embodiments, gastric retention is one week, two weeks, three weeks or one month or more.

In some embodiments of the disclosed devices, a portion of the device or the entire device is manufactured from the first enteric polymer.

In some embodiments of the disclosed devices, the pH insensitive polymer is positioned relative to the enteric polymer such that when the device is present in the gastric environment, the pH insensitive polymer is in contact with the gastric environment. In other embodiments, the pH insensitive polymer is present as at least a partial coating on a surface of the enteric polymer.

In various embodiments of the disclosed devices, the pH insensitive polymer is a non-ionic cellulose ester. In some embodiments, the pH insensitive polymer which may be a non-ionic cellulose ester coats at least at least 50% or at least 60% or at least 70% or at least 80% or at least 90% or at least 95% or at least 97% or at least 99% of the surface area of the enteric polymer.

In some embodiments of the disclosed devices, the first enteric polymer is a polymethacrylate-based copolymer. The polymethacrylate-based copolymer me be hydroxypropylmethylcellulose acetate succinate (HPMCAS). In some embodiments of the disclosed devices, the first enteric polymer includes one or more of HPMCAS-HG, HPMCAS-MG or HPLCAS LG. In various embodiments, the enteric polymer layer comprises HPMCAS-HG and HPMCAS-MG in a ratio of about 10:1 to about 1:1 or in a ratio of about 1:1, in a ratio of about 7:3, in a ratio of about 8:2, or in a ratio of about 10:1. In some embodiments, the enteric polymer layer comprises about 80% HPMCAS.

In some embodiments of the disclosed devices, the non-ionic cellulose ester is cellulose acetate. In some embodiments the coating consists essentially of cellulose acetate. In some embodiments, the cellulose acetate is present in an amount of about 30% to about 99% by weight of the solids in the coating. In various embodiments, the coating further comprises a second enteric polymer. The second enteric polymer may be hydroxypropylmethylcellulose acetate succinate (HPMCAS). In some embodiments, the HPMCAS is present in the amount of about 30% to about 70% by weight of the solids in the coating, about 30% to about 60% by weight of the solids in the coating, about 30% to about 50% by weight of the solids in the coating, about 40% to about 70% by weight of the solids in the coating, about 60% to about 70% by weight of the solids in the coating or about 50% to about 70% by weight of the solids in the coating.

In some embodiments of the disclosed devices, the coating further comprises a plasticizer. The plasticizer may be selected from triacetin, polyethylene glycol (PEG), dibutyl sebacate (DBS), or any combination thereof. In some embodiments, the plasticizer is PEG and PEG is present in the amount of about 0.5% to about 3% by weight of the solids in the coating.

In some embodiments of the disclosed devices, the plasticizer includes both triacetin and polyethylene glycol present relative to each other in a ratio of about 0.3:1 to 1:0.3. In some embodiments of the disclosed devices, in the coating the ratio of enteric polymer:plasticizer is from about 3:1 to about 12:1 or about 6:1 to about 12:1.

In some embodiments of the disclosed devices the coating forming the device comprises about
  a) 10 parts of HPMCAS, from 0 to about 1 part triacetin, from 0 to about 1 part PEG, and from 0.5 to about 1.5 part DBS; or
  b) about 10 parts of HPMCAS, about 0.3 to about 0.6 parts triacetin, about 0.3 to about 1 part DBS and about 0.2 to about 1 parts PEG or about 0.8 to about 1.2 parts triacetin; or
  c) about 10 parts of HPMCAS and about 0.9 to about 1.5 parts PEG; or
  d) about 10 parts of HPMCAS and about 0.8 to about 1.2 parts DBS; or
  e) about 10 parts of HPMCAS and about 0.3 to about 1 parts DBS and 0.2 to about 1 parts of PEG.

In some embodiments of the disclosed devices, the device further comprising a includes a capsule or other wrapper or cover. In some embodiments capsule houses the device.

In some embodiments of the disclosed devices, the carrier portion comprises at least two subparts, each being formed from the material; the drug being present in the carrier portion in the form of a depot structure positioned within at least one of the subparts of the carrier portion, wherein the subparts of the carrier portion are configured to separate when at least 50% of the depot structure dissolves due to release of the drug into the subject's stomach. In some embodiments of the disclosed devices, as shown in FIG. 7, the carrier portion 2 may comprise a first arm 4 and a second arm 6. In these embodiments and others, the carrier portion may be coated with a polymer coating on its outer surface, and at least one of the arms may be configured to release the active or diagnostic agent into a subject's gastric environment following administration of the device to the subject.

In another aspect, provided herein are methods of manufacturing a gastric retentive device as disclosed herein comprising providing a gastroretentive dosage form (GRDF); providing an enteric polymer layer which forms the carrier portion; and, coating the carrier portion with a pH insensitive polymer.

In yet another aspect, provided herein are methods of providing extended release of an active or diagnostic agent in a subject comprising orally administering a gastric retentive device as disclosed herein, thereby providing extended release of the agent.

In some embodiments of the methods, device is housed within a capsule prior to the oral administration, and the capsule dissolves within the subject's stomach when exposed to the stomach's milieu following delivery of the device thereto.

In another aspect, the present disclosure provides methods for manufacture of a device as disclosed herein, comprising forming a pellet by hot melt extrusion, the pellet comprising the enteric polymer; forming by injection molding at least two subparts of a carrier portion of the device; and, coating a surface of at least one of the subparts of the carrier portion of the device with the pH insensitive polymer.

In some embodiments the methods further comprise the steps of loading one or more of the subparts with a drug depot structure; and, assembling the subparts of the carrier portion in order to form the device.

In an embodiment of the devices and methods provided herein, the subject is a domestic or farm animal, a non-human primate or preferably a human.

The present disclosure provides oral pharmaceutical devices for delivering an active or diagnostic agent to a human subject's gastric environment, the devices comprising a material that comprises an enteric polymer and, optionally, a pH insensitive polymer such as a non-ionic cellulose ester, and being configured for gastric or intestinal retention for a period optionally of at least six hours when the subject is in the fed state; or, at least three hours in the fasted state and to release said active or diagnostic agent wherein any one or more of the following occur:
  a. the release of active or agent occurs independently of degradation of the enteric polymer in the gastric environment.
  b. wherein the material acts as a carrier portion for transporting said drug to the stomach.

The present disclosure provides oral pharmaceutical devices for delivering an active or diagnostic agent to a human subject's gastric environment, the devices comprising a material that comprises an enteric polymer and, optionally, pH insensitive polymer such as a non-ionic cellulose ester, and said device being configured:
  a. for gastric retention for an extended period preferably of at least six hours when the subject is in the fed state; or, at least three hours in the fasted state
  b. and to release said active or diagnostic agent
wherein the release of active or diagnostic occurs independently of the material's degradation in the gastric environment.

In a similar embodiment, the present disclosure provides oral pharmaceutical devices or components of devices for delivering an active or diagnostic agent to a human subject's gastric environment, the devices comprising a material that comprises an enteric polymer and a pH insensitive polymer such as a non-ionic cellulose ester, and being configured for gastric retention and to release said active or diagnostic agent wherein the release of the active or diagnostic agent is independent of dimensional and structural integrity of the component comprising active/diagnostic.

In some embodiments, release comprises release of the active or diagnostic agent into gastric fluid of the subject over said period.

In some embodiments, the material provides structural integrity for retention of the device or the agent or both in the stomach. In some embodiments, the material provides structural integrity, dimensional integrity, or both, in the gastric environment, and degradability in the intestinal environment. In some embodiments, the material provides reduced breakage during assembly, structural integrity over time in the upper GI environment and, reduced swelling or change in size over time in the upper GI environment. Despite the above, the material maintains the biodegradable nature of the enteric polymer.

In some embodiments, the release of active or diagnostic agent occurs independently of degradation of the material in the gastric environment.

In some embodiments the active or diagnostic agent is released in the gastric environment, in the intestinal environment or in both the gastric environment and the intestinal environment.

In an alternative embodiment, the present disclosure provides oral pharmaceutical devices for delivering an active or diagnostic agent and being configured for gastric retention for a period of at least three, or 5, 7, 9, 12 or 18 hours in the fasted state or six, 8, 10, 12, 14, 18, 24, 36 or 72 hours in the fed state and being configured to release the active or diagnostic agent into gastric fluid of the subject over said period, the devices comprising a material that comprises an enteric polymer, said gastric retentive structure maintaining its structural integrity while in the gastric environment for a desired period of time.

Also disclosed are uses of a material in the formation of a device configured for gastric retention or component thereof, said material having degradability in the intestine or high pH environment such as at greater than pH 6 as well as structural durability or dimensional integrity.

Also disclosed are methods for providing extended release of an agent within a subject comprising orally administering to the subject a device comprising a material that comprises an enteric polymer, and being configured for gastric retention for a period of at least six hours (three hours when the subject is in the fasted state) while maintaining its structural integrity and being configured to release the active or diagnostic agent into gastric fluid of the subject over the period, wherein the release occurs independently of any substantial degradation of the enteric polymer in the gastric environment.

The present disclosure also concerns uses of a material comprising an enteric polymer in the formation of a device configured for oral administration and for gastric retention while maintaining its structural integrity while in the gastric environment of a human, wherein the device releases or holds an active or diagnostic agent over an extended period of time in the gastric environment without significant degradation of the enteric polymer forming the material. In one embodiment, significant degradation is such that structural integrity or dimensional integrity are not maintained, for example, under simulated gastric conditions for 24 hours.

Also provided are methods for making a device for providing extended release of an active or diagnostic agent in the gastric environment of a human subject via oral administration comprising forming the device using a material that comprises an enteric polymer, the device being configured for gastric retention while maintaining its structural integrity while in the gastric environment; and, loading the device with the agent such that the agent is released over a period of at least six hours (three hours when the subject is in the fasted state) without any significant degradation of the enteric polymer in the gastric environment.

In certain embodiments, the present devices for providing extended release of a drug within a subject comprise a carrier portion for transporting said drug to the stomach of the subject via oral administration, the carrier portion may comprise at least two subparts, each being formed from a material that resists degradation within the stomach for at least six hours (three hours when the subject is in the fasted state), and, the carrier portion being configured to resist passage through the subject's pylorus absent physical separation of the subparts from each other (i.e., the subparts may be sized to permit individual passage through the pylorus), the drug being present in the carrier portion in the form of a depot structure positioned within at least one of the subparts of the carrier portion, wherein the subparts of the carrier portion are configured to separate when at least 50% of the depot structure is dissolved due to release of the drug into the subject's stomach; and, a coating on the outer surface of the carrier portion, wherein delivery of the device to the subject's stomach exposes at least a portion of the depot structure to the subject's gastric fluid such that the depot structure releases the drug into said fluids for a period of at least or about six hours (three hours when the subject is in the fasted state). Also disclosed are methods comprising orally administering these embodiments to a human subject.

The present disclosure also pertains to methods for making a device for providing extended release of a drug within a subject comprising forming a pellet by hot melt extrusion, the pellet comprising a material that resists degradation within a subject's stomach for at least six hours (three hours when the subject is in the fasted state); optionally forming by injection molding at least two subparts of a carrier portion of the device; coating a surface of at least one of the subparts of the carrier portion of the device; loading one or more of the subparts with a drug depot structure; and, assembling the subparts of the carrier portion in order to form the device.

DETAILED DESCRIPTION OF ILLUSTRATIVE EMBODIMENTS

Figure 1:
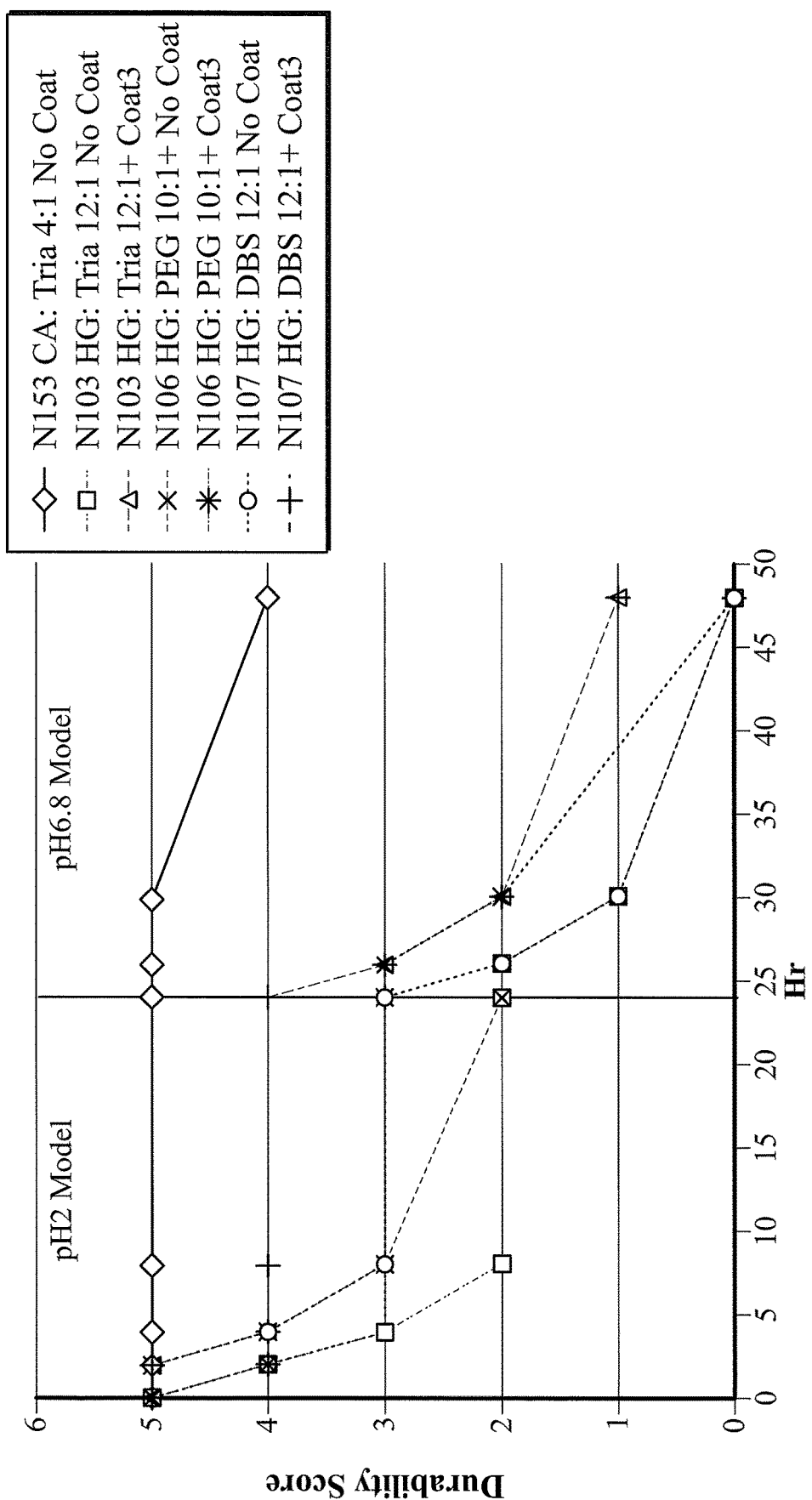
FIG. 1 is a graphical depiction of the durability scores over time of various polymer compositions, with or without plasticizer, and with or without a coating composition.

It is to be understood that the terminology used herein is for the purpose of describing particular aspects only and is not intended to be limiting. As used in the specification and in the claims, the term "comprising" can include the embodiments "consisting of" and "consisting essentially of." Unless defined otherwise, all technical and scientific terms used herein have the same meaning as commonly understood by one of ordinary skill in the art to which this disclosure belongs. In this specification and in the claims which follow, reference will be made to a number of terms which shall be defined herein.

As used in the specification and the appended claims, the singular forms "a," "an" and "the" include plural equivalents unless the context clearly indicates otherwise. Thus, for example, reference to "an enteric polymer" can include mixtures of two or more enteric polymers.

Ranges can be expressed herein as from one particular value, and/or to another particular value. When such a range is expressed, another aspect includes from the one particular value and/or to the other particular value. Similarly, when values are expressed as approximations, by use of the antecedent "about", it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if "10 to 15" is disclosed, then 11, 12, 13, and 14 are also disclosed.

As used herein, the term "material" is a composition which makes up a portion, element, component, or the like, of, for example, a gastric retentive device.

As used herein "structural integrity" refers to the ability of a gastroretentive dosage form (GRDF) or part thereof (e.g., carrier portion) to maintain its rigidity after exposure to certain conditions, for example mechanical and or physiological conditions. For example, a material according to the present disclosure is said to maintain its structural integrity when it evinces no or a minimal degree of swelling, shrinking, or softening during a desired period of time. The material disclosed herein maintains structural integrity in the gastric environment, which provides both mechanical (e.g. churning, flow) and physiological (e.g. low pH, bile gastric enzymes) challenges.

As used herein "dimensional integrity" refers to the ability of a material to maintain one or more of its size dimensions after exposure for a period to a mechanical or physiological conditions (e.g., gastric contractions and or pH<3). For example, dimensional integrity may be characterized as when a material loses less than 20% of its size (i.e., in one or more geometric dimensions), less than 18% of its size, less than 16% of its size, less than 14% of its size, less than 12% of its size, preferably less than 10% of its size, less than 8% of its size, less than 6% of its size, less than 5% of its size, less than 4% of its size, less than 3% of its size, less than 2% of its size, or less than 1% of its size over the period. The opposite condition of dimensional integrity may be referred to as geometric deformation. Geometric deformation of a material may be characterized, for example, by change in any geometric dimension or configuration of the material from its original state in the device in which the material is present. When geometric deformation of material is minimal or low, the material may be said to possess dimensional integrity.

The term "gastric environment" refers to the conditions in the stomach. The stomach, for example, provides for mechanical and chemical digestion of food via presence of gastric juices, bile, and the like.

As used herein "degradability" refers to the ability of a device (e.g., GRDF) to lose structural integrity under certain physiologic conditions in the body such that the degradation products are excretable and/or absorbable by the body. In some embodiments, a device having structural integrity in the stomach or simulated gastric conditions also has low degradability in the stomach or simulated gastric conditions. A device with low structural integrity may be characterized by relatively high degradability in the stomach or simulated conditions.

As referred to herein "gastric retention" or "gastric retentive" refers to the ability of a device (e.g., GRDF) to be maintained in the gastric environment for a period of time. Preferably the device retains structural integrity in the gastric environment for the majority of the time it is gastric retentive.

As used herein, the term "collapsed configuration" of a GRDF is the state of the device prior to ingestion where the GRDF is a size that is suitable for swallowing. "Collapsed" may refer to closed, nested, contracted, compressed, or the like.

As used herein, the "expanded configuration" of the GRDF is the state of the device following ingestion and following entry to the gastric environment that is capable of maintaining the GRDF in the stomach (gastric retention) and preventing passage through the pyloric valve. "Expanded" may refer to opened, telescoped, or the like.

As used herein, the term "carrier portion" refers to an encasement or subunit configured to hold or house an API, diagnostic agent, or both, for release in the upper gastrointestinal environment.

As used herein, the terms "about" and "at or about" mean that the amount or value in question can be the value designated some other value approximately or about the same. It is generally understood, as used herein, that it is the nominal value indicated±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

Disclosed are the materials to be used to prepare the devices of the disclosure as well as the devices themselves, methods for preparing such devices, and methods involving the use of such devices. It is understood that when combinations, subsets, interactions, groups, etc. of materials are disclosed that while specific reference of each various individual and collective combinations and permutation of these materials cannot be explicitly disclosed, each is specifically contemplated and described herein. For example, if a particular material is disclosed and discussed and a number of modifications that can be made to a number of components are discussed, specifically contemplated is each and every combination and permutation of the material and the modifications that are possible unless specifically indicated to the contrary. Thus, if a class of materials A, B, and C are disclosed as well as a class of materials D, E, and F and an example of a combination, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the devices of the disclosure. Thus, if there are a variety of additional steps that can be performed it is understood that each of these additional steps can be performed with any specific aspect or combination of aspects of the methods of the disclosure.

All cited patents, patent applications, and other references are incorporated herein by reference in their entirety.

While typical embodiments have been set forth for the purpose of illustration, the foregoing descriptions should not be deemed to be a limitation on the scope herein. Accordingly, various modifications, adaptations, and alternatives can occur to one skilled in the art without departing from the spirit and scope herein.

The present disclosure provides devices that are configured for gastric retention for a period greater than that typical of oral pharmaceuticals, while maintaining their structural integrity and releasing an active or diagnostic agent into gastric fluid of a human subject over that period, as well as methods of delivering the agent over an extended period by orally administering such devices to a subject, uses of an enteric polymer in the formation of devices that deliver an agent over an extended period of time, and methods of making such devices. For example, said period of time may be at least six hours, eight hours, 10 hours, 12 hours, 18 hours, or 24 hours in the fed state, or at least three hours, five hour, six hours, eight hours, 10 hours, 12 hours, 18 hours, or 24 hours when the subject is in the fasted state.

Although gastric retentive devices are generally known, improvements are required with respect to the materials suitable for maintaining structural and geometric integrity of devices in situ, including the ability of such devices to withstand for an extended period of time the harsh physical challenges presented by the gastric environment, and, at the same time, with respect to whether the devices are made using materials that are readily available, pharmaceutically acceptable, and easily processed into desired configurations that are tunable according to the identity of the agent to be delivered and the required release profile. The present inventors have discovered that devices for retention in the gastric environment that comprise a material comprising an enteric polymer and a non-ionic cellulose ester, and that are configured to release or hold a drug or diagnostic agent independently of any degradation of such polymers while in the gastric environment, can fulfill each of these traditional needs. The inventive devices can be used to hold an active or diagnostic agent or to deliver such an agent at a controlled rate over a period of three hours to 24 hours, and during the release period, the devices retain their structural integrity and remain durable even under human gastric conditions. At the same time, the devices are configured so that they can be orally administered, for example, within a standard capsule shell. Additionally, the ability of the inventive devices to retain their structural integrity within the gastric environment during a desired release/holding period is strikingly contrasted by the ability of the devices to pass from the stomach following the desired period, resulting in quick and complete degradation within the lower gastrointestinal tract. These and other advantages are readily apparent from the instant disclosure.

Accordingly, provided are devices for delivering an active or diagnostic agent to a human subject's gastric environment via oral administration, each of such devices comprising a material that comprises an enteric polymer and a non-ionic cellulose acetate, and being configured for gastric retention for a period of at least six hours (three hours when the subject is in the fasted state) while maintaining its structural integrity and to release the active or diagnostic agent into gastric fluid of the subject over said period, wherein the release occurs independently of any degradation of the material in the gastric environment.

With respect to the presently disclosed materials (including aspects of the instant devices or components of devices that are formed using such materials), dimensional integrity or loss of detail over time in the gastric environment can be quantified using assays known in the art. In some embodiments, dimensional integrity or loss of detail over time is measured using an in vitro model. Dimensional integrity can be measured using the "dimensional integrity test" as described in Example 3, infra, by placing the Type A component (hereafter, the "test sample") into a pharmacopoeia dissolution apparatus II, 400 mL, at 37° C., 100 RPM, containing 0.1 N HCl+Xanthan 0.125 g/L for 24 hours. At t=0, 4, 8, and 24 hours, the width (W) of the test sample is measured. The percentage change in width is calculated as [Absolute Value $(W_t-W_0)]/W_0]\times 100$ wherein $W_t$ is the width at t hr and $W_0$ is the width at t=0. In certain embodiments, the dimensional integrity of a test sample, measured as the percentage change in width at 24 hours, is less than 10%, less than 7%, less than 5%, less than 3%, or less than 2%.

In certain instances, the structural integrity of the presently disclosed materials (including aspects of the instant devices that are formed using such materials) over time in the stomach environment can be quantified using the rigidity [1] test, as described in Example 3, infra. In certain embodiments, the measured structural integrity of a test sample is at least 60%, at least 80%, or at least 100%, as measured by the rigidity [1] test at 24 hours, of the value measured at t=0.

As used herein, intestinal degradability can be quantified using the rigidity [2] test, described in Example 3, infra. A lower the value refers to a less rigid device and higher degradation. In certain embodiments, intestinal degradability of a test sample (e.g., GRDF or component thereof) is less than 60%, less than 40%, less than 20%, or about 0%, as measured by the rigidity [2] test at t=24 hours, relative to the value at t=0. In other embodiments, the degradability is less than 65%, less than 35%, or less than 10%, as measured by the rigidity[2] test at t=8 hours, relative to the value at t=0.

As used herein, "active or diagnostic agent" is meant to include any substance relevant for gastric retention as recognized in the art, and is abbreviated herein as "API". A wide variety of APIs (which may be therapeutic, diagnostic or otherwise beneficial) may be employed in accordance with the aspects of the present disclosure. Any API which is relevant for gastric retentive delivery or as a diagnostic known in the art is intended to be encompassed by the present disclosure. Relevant APIs may include, but are not limited to, the following: APIs acting locally in the stomach; APIs primarily absorbed in the stomach; APIs poorly soluble in alkaline pH; APIs with narrow windows of absorption; APIs absorbed rapidly from the gastrointestinal (GI) tract; APIs that degrade in the colon; and APIs that disturb colonic microbes.

Active pharmaceutical ingredients (APIs) may include but are not limited to the following: prochlorperazine edisylate, ferrous sulfate, albuterol, aminocaproic acid, mecamylamine hydrochloride, procainamide hydrochloride, amphetamine sulfate, methamphetamine hydrochloride, benzphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, metformin, methylphenidate hydrochloride, theophylline cholinate, cephalexin hydrochloride, diphenidol, meclizine hydrochloride, prochlorperazine maleate, phenoxybenzamine, thiethylperazine maleate, anisindione, diphenadione erythrityl tetranitrate, digoxin, isoflurophate, acetazolamide, nifedipine, methazolamide, bendroflumethiazide, chlorpropamide, glipizide, glyburide, gliclazide, tobutamide, chlorproamide, tolazamide, acetohexamide, troglitazone, orlistat, bupropion, nefazodone, tolazamide, chlormadinone acetate, phenaglycodol, allopurinol, aluminum aspirin, methotrexate, acetyl sulfisoxazole, hydrocortisone, hydrocorticosterone acetate, cortisone acetate, dexamethasone and its derivatives such as betamethasone, triamcinolone, methyltestosterone, 17-β-estradiol, ethinyl estradiol, ethinyl estradiol 3-methyl ether, prednisolone, 17-β-hydroxyprogesterone acetate, 19-nor-progesterone, norgestrel, norethindrone, norethisterone, norethiederone, progesterone, norgesterone, norethynodrel, terfandine, fexofenadine, aspirin, acetaminophen, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, selegiline, chlorpromazine, methyldopa, dihydroxyphenylalanine, calcium gluconate, ketoprofen, ibuprofen, cephalexin, erythromycin, haloperidol, zomepirac, ferrous lactate, vincamine, phenoxybenzamine, diltiazem, milrinone, captropril, mandol, quanbenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinopril, enalapril, captopril, ramipril, enalaprilat, famotidine, nizatidine, sucralfate, etintidine, tetratolol, minoxidil, chlordiazepoxide, diazepam, amitriptyline, and imipramine, and pharmaceutical salts of these active agents. Further examples are proteins and peptides which include, but are not limited to, cyclosporins such as cyclosporine A, insulin, coichicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatropin, oxytocin, vasopressin, prolactin, somatostatin, lypressin, pancreozymin, luteinizing hormone, LHRH, interferons, interleukins, growth hormones such as human growth hormone, bovine growth hormone and porcine growth hormone, fertility inhibitors such as the prostaglandins, fertility promoters, growth factors, and human pancreas hormone releasing factor.

As used herein, the term "upon exposure to gastric fluid" can to be taken literally, or when needed, can refer to a suitable model simulating gastric conditions.

As used herein, the term "pharmaceutically acceptable" refers to a material that is not biologically or otherwise unacceptable when used in the invention. For example, the term "pharmaceutically acceptable carrier" refers to a material that can be incorporated into a composition and administered to a patient without causing unacceptable biological effects or interacting in an unacceptable manner with other components of the composition. Such pharmaceutically acceptable materials typically have met the required standards of toxicological and manufacturing testing, and include those materials identified as suitable inactive ingredients by the U.S. Food and Drug Administration.

In some embodiments, the present devices are formed at least in part using materials that include an enteric polymer and a non-ionic cellulose ester.

In the devices, the material may form a subpart of the device that represents a gastroretentive mechanism. Various retentive mechanisms are described more fully infra. Alternatively or additionally, the material forms a subpart of the device that houses the active or diagnostic agent, permits controlled release of the active or diagnostic agent, or both.

As used herein, the phrase "enteric polymer" refers to a polymer that does not readily dissolve or degrade under the typical pH and other physical conditions of a human stomach, but that does dissolve or degrade at pH and other physical conditions of the intestinal tract of a human, i.e., the conditions that exist following passage from the stomach through the pylorus (i.e. pH>5). When the singular form of "enteric polymer" is used, this can refer to one enteric polymer, a mixture of two or more enteric polymers, or a mixture of polymers of which at least one is an enteric polymer, as long as the resulting mixture is enteric in nature. Any pharmaceutically acceptable enteric polymer that provides the material that is used in forming the present devices may be used, provided that it confers the ability to be retained in the gastric environment for a period of at least six hours (or three hours when the subject is in the fasted state) while maintaining its structural integrity, as well as the ability to degrade within the intestinal tract, or alternatively, the lower intestinal tract of a human.

In some embodiments, dimensional integrity may be characterized by less than a 10% change in width as measured after 24 hours in a pharmacopoeia dissolution apparatus II, 400 mL, at 37°, 100 RPM, HCl 0.1N+Xanthan 0.125 g/L, relative to the width measured at t=0 (see Example 3, infra). In certain instances, structural integrity may be characterized by retaining at least 60% of its original rigidity as measured by the rigidity [1] test (as described in Example 3, infra). In some embodiments, the degradability of a material may be characterized by retaining less than 60% of its original rigidity as measured by the rigidity [2] test (as described in Example 3, infra).

Swelling or shrinking may be characterized as minimal when the device swells or shrinks by no more than 30%, no more than 20%, no more than 10%, no more than 9%, no more than 8%, no more than 7%, no more than 6%, no more than 4%, no more than 3%, no more than 2%, or no more than 1% of its original volume. Geometric deformation may be characterized as minimal when the device maintains the functionalities of gastric retention, release of API, or both, within the desired period of time. Geometric deformation is more than minimal when one or both of such functionalities is compromised. For example, if the device comprises an assembly of multiple subparts, and if it is necessary for each of the subparts to be joined in order for the device to be gastrically retained, or to release API, any geometric deformation that results in at least partial separation of one of the subparts from the other subpart(s), or that results in any decrease or interruption of release of API, cannot be characterized as minimal. At the same time, a device according to the present disclosure can be said to maintain its structural integrity in the gastric environment even though it dissolves, degrades, or deforms upon exposure to an medium at pH 6-7, such as within the human intestinal tract or in a simulated intestinal environment.

The enteric polymer may be a polymethacrylate-based copolymer, i.e., a copolymer of polymethacrylate and another monomer component. In some embodiments, the enteric polymer comprises hydroxypropylmethylcellulose acetate succinate (HPMCAS), also referred to as hypromellose acetate succinate. The enteric polymer may be at least about 90% HPMCAS. For example, the enteric polymer may be more than 90% HPMCAS. The enteric polymer may be HPMCAS-HG, HPMCAS-MG, HPMAS-LG or a combination thereof. In certain embodiments, the enteric polymer comprises both HPMCAS-HG and HPMCAS-MG in a ratio of about 10:1 to about 1:5. For example, the enteric polymer may comprise HPMCAS-HG and HPMCAS-MG in a ratio of about 1:5, about 1:4, about 1:3, about 1:2, about 1:1, about 2:1, about 3:1, about 3:2, about 4:1, about 4:3, about 5:1, about 5:2, about 5:3, about 5:4, about 6:1, about 6:5, about 7:3, about 7:4, about 7:5, about 7:6, about 8:1, about 8:2, about 8:3, about 8:5, about 8:7, about 9:1, about 9:2, about 9:4, about 9:5, about 9:6, about 9:7, about 9:8, or about 10:1.

The material that is used in forming the device may also include one or more plasticizers. For example, the material may be one or more plasticizers in combination with an enteric polymer. Non-limiting examples of suitable plasticizers include dibutyl sebacate, triacetin, triethyl-citrate, acetyl tributyl citrate, acetyl triethyl citrate polyethylene glycol, polyethylene glycol monomethyl ether, glycerin, sorbitol sorbitan solutions, castor oil, diacetylated monoglycerides, triethyl citrate, tributyl citrate or others. In some embodiments, the plasticizer is triacetin, polyethylene glycol (PEG), dibutyl sebacate (DBS), or any combination thereof. The plasticizer may include both triacetin and polyethylene glycol are present relative to each other in a ratio of about 0.1:1 to 1:0.1.

In the present materials, the ratio of enteric polymer: plasticizer may be from about 4:1 to about 15:1. For example, the ratio of enteric polymer to plasticizer may be about 4:1, about 5:1, about 6:1, about 7:1, about 8:1, about 9:1, about 10:1, about 11:1, about 12:1, about 13:1, about 14:1, or about 15:1. In certain embodiments, the ratio of enteric polymer: plasticizer is about 6:1 to about 12:1.

Certain embodiments are such that the material that is used in the formation of the device comprises HPMC-AS and one or more of triacetin, PEG, and DBS. For example, the material may include about 10 parts of HPMC-AS, from 0 to about 1.5 part triacetin, from 0 to about 1.5 part PEG, and from 0 to about 1.5 part DBS. The material that is used in the formation of the device may alternatively comprise about 10 parts of HPMC-AS, about 0.4 to about 0.5 parts triacetin, and about 0.7 to about 0.9 parts PEG. In another instance, the material that is used in the formation of the device comprises about 10 parts of HPMC-AS and about 0.8 to about 1.2 parts triacetin. In other embodiments, the material that is used in the formation of the device comprises about 10 parts of HPMC-AS and about 0.9 to about 1.5 parts PEG. In yet other embodiments, the material forming the device comprises about 10 parts of HPMC-AS and about 0.8 to about 1.2 parts DBS.

The material that is used in the formation of the device may, in addition to the enteric polymer, further comprise a pH insensitive polymer such as a non-ionic cellulose ester. An example of a non-ionic cellulose ester includes cellulose acetate, and those of ordinary skill in the art can readily identify alternative examples of such compounds. In some embodiments, the enteric polymer and the pH insensitive polymer such as the non-ionic cellulose ester are present as separate layers. In such embodiments, each layer may house or contain a therapeutic or diagnostic agent. In certain other examples, the pH insensitive polymer may be on an external surface or on a face of the device or component of the device that is otherwise directly exposed to gastric conditions. In certain other embodiments, the non-ionic cellulose ester is present as a coating on a surface of the enteric polymer. For example, when the enteric polymer is HPMC-AS, the non-ionic cellulose ester may be present as a coating on a surface of the enteric polymer. The present inventors have discovered that a coating of non-ionic cellulose ester on a surface of an enteric polymer enhances the ability of the inventive devices to maintain their structural integrity, as characterized above, in the gastric environment for an extended period of time, without significantly affecting the devices' ability to disintegrate in the intestine or the lower gastrointestinal tract, and without significant increase of brittleness of the devices. The coating of the pH insensitive polymer of non-ionic cellulose ester may be present on one, more than one, or all outer surfaces of the enteric polymer. The coating may cover more than 50%, more than 60%, more than 70%, more than 80% or more than 90% of the surface area exposed to the gastric environment. The coating may be applied by dipping, spray drying, or any other technique. The thickness of the coating is preferably constant along a given surface and, when multiple surfaces are coated, among each of the multiple surfaces. The thickness of the coating may be from about 10 µm to about 200 µm. For example, the coating may have a thickness of about 10 µm, about 20 µm, about 50 µm, about 60 µm, about 70 µm, about 80 µm, about 90 µm, about 100 µm, about 120 µm, about 140 µm, about 150 µm, about 160 µm, about 170 µm, about 180 µm, about 190 µm, or about 200 µm. The percent weight gain of the device as a result of the coating may be from about 1 to about 10, about 2 to about 7, or about 3 to about 5.

The pH insensitive polymer such as the non-ionic cellulose ester should be compatible with the enteric polymer. In some embodiments, the non-ionic cellulose ester is cellulose acetate, which may be present in the amount of about 30 to about 99% by weight of the solids in the coating. When the non-ionic cellulose ester is present as a coating, the coating may further include an enteric polymer such as hydroxypropylmethylcellulose acetate succinate (HPMC-AS). In addition, it may further comprise polyethylene glycol (PEG). The ratio of pH insensitive polymer such as the non-ionic cellulose ester to enteric polymer may be in a ratio of 99.5:0.5 to about 70:30 such as about 99.5:0.5, 95:5, 80:20, or 70:30. HPMC acetate succinate may be HPMCAS-HG, HPMCAS-MG, HPMCAS-LG, or any combination thereof. Preferably, the HPMC acetate succinate is HPMCAS-MG or HPMCAS-HG, most preferably HPMCAS-HG. When present, the PEG may be present in the amount of about 0.2 to about 5% or 0.5 to 3% by weight of the solids in the coating.

The present devices may have any physical configuration that is compatible with certain basic functionalities. First, it should be compatible with being orally administered to a human. For example, it can be housed within a capsule that is sized and shaped for oral administration, that substantially maintains its integrity prior to entry into the stomach, but that dissolves immediately or shortly after (e.g., within 1 hour) exposure to gastric conditions. Second, it should be compatible with being retained within the stomach (i.e., does not pass through the pylorus) for a desired period of time, such as for at least six hours or at least three hours when the subject is in the fasted state. Third, it should be capable of releasing API into the gastric environment for an extended period of time, in a desired release profile. For example, the API may be released at a controlled rate, such as a constant rate, at a descending rate, or at an ascending rate, over time. Fourth, following expiration of the desired release period, the device is no longer retained within the desired location and passes through the pylorus, either in its original form or in two or more subparts that have at least partially separated from one another or are spatially oriented relative to one another in a different manner than they were during the release period. Because the device comprises a material that includes an enteric polymer, passage of the device or subparts thereof out of the gastric environment (through the pylorus) results in more rapid breakdown and ultimate disintegration of the device or subparts thereof in the intestinal tract. In preferred embodiments, other than any residual API that was not released in the gastric environment, the present devices do not contain any significant amount of diagnostic or active agent for release in the portion of the gastrointestinal tract beyond the pylorus. In some embodiments, the device is shaped, sized, or both shaped and sized to resist passage through the subject's pylorus, prior to release of at least 40%. 50%, at least 70%, at least 80%, at least 90%, or at least 95% of the agent that is present in the device prior to administration to the patient. For example, the device may have a collapsed configuration when housed within a capsule prior to oral administration, and have an expanded configuration following dissolution of the capsule in the subject's stomach following oral administration, the expanded configuration being sized so as to prevent passage of the device through the subject's pylorus. Designs for collapsible and expandable devices of this type are disclosed in PCT/US2015/33850, filed Jul. 1, 2015, which is incorporated herein by reference in its entirety, and also disclosed in the Examples, below. Other configurations of devices having a compressed and an expanded configuration are contemplated by the present disclosure. For example, the device may have a spring-like configuration, an accordion-like configuration, a clamshell configuration, a scissor-like configuration, a telescope-like configuration, or any other suitable configuration. In some embodiments, the material that is used in the formation of the device is shaped, sized, or both shaped and sized to resist passage through the subject's pylorus. In other embodiments, another portion of the device is configured to resist passage through the pylorus.

In other embodiments, the device has one or more other properties that prevent passage through the pylorus prior to termination of the period during which release of API is desired. For example, the device may include a mucoadhesive agent that causes at least a portion of the device to adhere to an interior surface of the stomach wall. At the end of the desired API release period, the mucoadhesive property can be nullified, for example, by a chemically countermanding material, by forcible detachment of the device or a component thereof, by separation of the device into two or more parts, thereby weakening the ability of the device to adhere to the stomach wall, or by any other mechanism. This can occur, for example, following release of the at least 50%, at least 70%, or at least 90% of the agent, or, if expressed in terms of time, about three hours, about six hours, about eight hours, about 10 hours, about 12 hours, about 14 hours, about 16 hours, about 18 hours, about 20 hours, about 22 hours, about 24 hours, about 28 hours, about 30 hours, about 32 hours, about 34 hours, about 36 hours, about 40 hours, about 44 hours, or about 48 hours following entry of the device into the subject's stomach after being orally administered. The device may use any other strategy for providing gastric retention as known in the art, such as floatation, expansion, or the like.

In other embodiments, following release of at least 50%, at least 70%, at least 80%, at least 90%, or at least 95% of the agent, or following any of the periods of time recited in the preceding paragraph, the device can change its size and/or shape in a manner that permits passage of the device, or subparts thereof, through the pylorus. For example, at least one dimension of the device can change in order to permit passage through the pylorus. This can occur by a change in configuration, such as by a change in the spatial orientation of at least two subparts of the device relative to one another. In other embodiments, there are no subparts to the device, and the change occurs by the flattening, shortening, narrowing, contraction, or any other change in size or shape. In other embodiments, the device can separate into two or more subparts that are individually capable, by virtue of size or shape, through the pylorus. In any of the preceding embodiments, the device may include one or more predefined apertures through which the agent is released into the gastric fluid. For example, administration of the device exposes at least a portion of the agent to the subject's gastric fluid such that the device releases the agent through one or more predefined apertures into the fluid. The material that is used in the formation of the device may include one or more of such predefined apertures. In other embodiments, another portion of the device includes one or more of the apertures. The aperture may be a pore, a hole, a channel, a screen, or any other opening that permits release of the agent into the gastric fluid. Preferably, the aperture defines a surface area of the API that is exposed to the gastric fluid, and determines the amount and thereby rate of release of the API into the gastric environment. The amount of API that is exposed to the gastric fluid may be constant over time, thereby resulting in a constant rate of release. As is readily appreciated by those of ordinary skill in the art, the appropriate release profile is defined by the treatment regimen and type of API being administered.

The period of time during which the device releases the agent into the fluid may be about three hours, about six hours, about eight hours, about 10 hours, about 12 hours, about 14 hours, about 16 hours, about 18 hours, about 20 hours, about 22 hours, about 24 hours, about 28 hours, about 30 hours, about 32 hours, about 34 hours, about 36 hours, about 40 hours, about 44 hours, about 48 hours, about 60 hours, or about 72 hours following entry of the device into the subject's stomach after being orally administered. Release of API from the present devices may occur independently of any degradation of the enteric polymer in the gastric environment. This means, inter alia, that release of API is unrelated to whether or not any of the enteric polymer in the material that forms is used in the formation of the device degrades in the gastric environment. Thus, release of API can occur by a mechanism other than degradation of any portion of the material that is used in the formation of the device.

In many conventional devices that are configured to release API in the stomach, it is necessary for some portion of the device, such as a coating, a wall, or an aperture plug to dissolve in the gastric environment before drug can be released. In contrast, release of API from the instant devices can commence upon exposure of the instant devices to gastric fluid. For example, release of API from the device commences substantially immediately (e.g., within about 15 minutes, about 12 minutes, about 10 minutes, about 8 minutes about 6 minutes, about 5 minutes, about 4 minutes, about 3 minutes, about 2 minutes, or about 1 minute or less) following exposure of the device to gastric fluids. When the device is orally administered within a capsule that dissolves in gastric fluids, exposure of the device to gastric fluids will occur when the capsule is breached by the gastric fluids. When the device comprises one or more predefined apertures, exposure of API to gastric can occur by penetration of the aperture(s) by the gastric fluids. Accordingly, the present devices are such that exposure and thereby release of API to gastric fluids does not involve removal by degradation of any part of the device.

In certain embodiments, the present devices for providing extended release of a drug within a subject comprise a carrier portion for transporting said drug to the stomach of the subject via oral administration, the carrier portion may comprise at least two subparts, each being formed from a material that resists degradation within the stomach for at least six hours (three hours when the subject is in the fasted state), and, the carrier portion being configured to resist passage through the subject's pylorus, absent physical separation of the subparts from each other, the drug being present in the carrier portion in the form of a depot structure positioned within at least one of the subparts of the carrier portion, wherein the subparts of the carrier portion are configured to separate when at least 50% of the depot structure is dissolved due to release of the drug into the subject's stomach; and, a coating on the outer surface of the carrier portion, wherein delivery of the device to the subject's stomach exposes at least a portion of the depot structure to the subject's gastric fluid such that the depot structure releases the drug into said fluids, respectively, for a period of at least or about six hours (three hours when the subject is in the fasted state).

In such embodiments, the subparts may be configured to separate when at least 60%, about 65%, about 70%, about 75%, about 80%, about 85%, about 90%, or more than about 90% of the depot structure is dissolved.

These devices may include one subpart, two subparts, three subparts, four subparts, five subparts, or more than five subparts. When more than two subparts are present, the expression "wherein the subparts of the carrier portion are configured to separate" means that the device is such that at least one of the subparts is configured to separate from the other subparts.

In the embodiments of the present devices having subparts, the devices may have a compressed configuration when housed within a capsule prior to oral delivery, and an expanded configuration following dissolution of the capsule in the subject's stomach, following oral delivery, the expanded configuration being sized so at to prevent passage of the device through the subject's pylorus. In certain embodiments of such devices, the subparts can include a hinge piece, and first and second arm pieces that are both joined to the hinge piece, and wherein the first and second arm pieces are proximate to each other in the compressed configuration of the device, and are spaced apart from each other in the expanded configuration of the device. Exemplary designs of this type are disclosed in PCT/US2015/33850, filed Jul. 1, 2015, incorporated herein by reference. In these devices, the hinge piece may be configured to separate from the first and second arm pieces when at least 50%, at least 60%, about 65%, about 70%, about 75%, about 80%, about 85%, about 90%, or more than about 90% of the depot structure is dissolved due to release of the drug into the subject's stomach.

As noted above, the present devices are characterized by their ability to retain their structural integrity even after exposure to gastric conditions over an extended period of time. Some of the physical characteristics of exemplary devices according to the present invention are described in the Examples, infra.

The dimensional integrity test functions as an in vitro model for assessing loss of detail over time in stomach environment. In some embodiments, the dimensional integrity of the presently disclosed materials or component formed therefrom is less than 10%, less than 7%, less than 5% or less than 3% change in width at t=24 hours relative to the width of the material or component at t=0.

The rigidity[1] test functions as an in vitro model for assessing change in strength against deformation over time in stomach environment. In some embodiments, the structural integrity of the presently disclosed materials or component formed therefrom is at least 60%, at least 65%, at least 80% or at least 100% of original rigidity at t=24 hours as measured using the rigidity[1] test.

The rigidity [2] test functions as an in vitro model for assessing degradability in the intestine. In one embodiment, degradability (i.e., retention of original rigidity) of the presently disclosed materials or component formed therefrom in the intestinal environment as measured in the rigidity[2] test at t=24 hours may be less than 80%, more preferably less than 70%, more preferably less than 60%, more preferably less than 40%, more preferably less than 30%, more preferably less than 20%, more preferably less than 10%, more preferably about 0% of the original rigidity (t=0). In another embodiment, the material or component as measured at t=8 hours may be less than 65% or less than 35% of the original rigidity (t=0), as measured by the rigidity[2] test.

In some embodiments, the materials that are used in the formation of the present devices maintain their structural integrity under an applied force of about 150 to about 500 gram-force (~5 Newton) following exposure of the device for at least 24 hours to a fluid at pH 2, which can be said to simulate gastric conditions. For example, the materials that are used in the formation of the devices can maintain their structural integrity under an applied force of about 150 gf, about 200 gf, about 250 gf, about 300 gf, about 350 gf, about 400 gf, about 450 gf, or about 500 gf, following exposure of the device for at least 24 hours to a fluid at pH 2. In some embodiments, the materials that are used in the formation of the devices swell by no more than about 15% (i.e., as compared to the material's original volume when initially introduced into the gastric environment) as a result of exposure of the device for at least 24 hours to a fluid at pH 2. For example, the materials that are used in the formation of the devices can be characterized as swelling by no more than about 15%, by no more than about 9%, by no more than about 8%, by no more than about 7%, by no more than about 6%, by no more than about 4.5%, by no more than about 4%, by no more than about 3.5%, by no more than about 3%, by no more than about 2.5%, or by no more than about 2% as a result of exposure of the device for at least 24 hours to a fluid at pH 2. In some embodiments, the materials that are used in the formation of the devices possess a "deformation modulus" of about 75 to about 500 gf/mm following exposure of the device for at least 24 hours to a fluid at pH 2. For example, the materials that are used in the formation of the device may have a deformation modulus of about 75 gf/mm, about 100 gf/mm, about 125 gf/mm, about 150 gf/mm, about 175 gf/mm, about 200 gf/mm, about 225 gf/mm, about 250 gf/mm, about 275 gf/mm, about 300 gf/mm, about 325 g/mm, about 350 gf/mm, about 400 gf/mm, or about 450 gf/mm following exposure of the device for at least 24 hours to a fluid at pH 2.

Also disclosed herein are methods for providing extended release of an agent within a subject comprising orally administering to the subject a device in accordance with any of the embodiments described above in connection with the inventive devices.

Oral administration of the instant devices to a subject may follow any desired regimen. For example, a device according to the present disclosure may be administered to a subject once, twice, or several times daily, or may be administered once every two, three, four, five, six, seven, eight, nine, 10, 11, 12, 13, 14, or more than 14 days. The propriety of a particular regimen may be determined by the nature of the API in the device, the needs of the particular subject, and other factors that are readily understood among those skilled in the art.

The present disclosure also concerns uses of a material comprising an enteric polymer in the formation of a device configured for oral administration and for gastric retention while maintaining its structural integrity while in the gastric environment of a human, wherein the device releases an active or diagnostic agent is released over an extended period of time in the gastric environment without degradation of the material. In some embodiments, the material comprises the enteric polymer and a non-ionic cellulose acetate. In accordance with the present uses, the device, the materials from which it is formed, and the structural and functional characteristics of the device may be in accordance with any of the embodiments described above in connection with the inventive devices.

Also provided are methods for making a device for providing extended release of an active or diagnostic agent in the gastric environment of a human subject via oral administration comprising forming the device using a material that comprises an enteric polymer, the device being configured for gastric retention while maintaining its structural integrity while in the gastric environment; and, loading the device with the agent such that the agent is released over a period of at least six hours (three hours when the subject is in the fasted state) independently of any degradation of the material in the gastric environment.

In accordance with the present methods of making, the device, the materials from which it is formed, and the structural and functional characteristics of the device may be in accordance with any of the embodiments described above in connection with the inventive devices. In some embodiments, the material comprises the enteric polymer and a non-ionic cellulose acetate. The process of forming the device from the materials, including shaping the enteric polymer and any other materials that are mixed therewith (such as one or more plasticizers) and optionally coating the enteric polymer, may be completed using any appropriate manufacturing technique. For example, the device may be made by an injection molding technique, or by three-dimensional printing. The injection molding process may involve forming a pellet comprising material that includes the enteric polymer by hot melt extrusion, and injection molding the pellet into the device. When the device includes a coating of the type described above in connection with the inventive devices (e.g., a coating comprising a non-ionic cellulose acetate), the coating may be applied to a surface of the injection molded structure by dipping, spray drying, or any other acceptable technique.

In some embodiments, the devices are made by forming a pellet by hot melt extrusion, the pellet comprising a material that resists degradation within a subject's stomach for at least six hours (three hours when the subject is in the fasted state); forming by injection molding at least two subparts of a carrier portion of the device; coating a surface of at least one of the subparts of the carrier portion of the device; loading one or more of the subparts with a drug depot structure; and, assembling the subparts of the carrier portion in order to form the device.

In accordance with any of the preceding methods of making a device, the API is loaded into or onto the device or an independent subpart thereof following formation of the device or the subpart. When the device includes a coating, it is the case that either the coating is not applied in a manner that would prevent access to the API by gastric fluids when the device enters the subject's stomach, or the API is loaded into the device following coating, such that the coating does not represent a barrier between API and the ambient environment of the device (the gastric fluids when the device is in situ). Loading of the device into or onto the API may occur, for example, by injection of API into an aperture, by permitting the device to imbibe or absorb API, by incorporating a solid component containing the API onto or into the device or including the solid component containing API as a subpart of the device by assembling the solid component together with at least one other subpart of the device, or any other manner that permits administration of the API together with the device and release of the API from the device into the gastric environment.

Aspects

The present disclosure pertains to and includes at least the following aspects:

Aspect 1. A device for delivering an active or diagnostic agent to a human subject's gastric environment via oral administration, the device comprising a material that comprises a first enteric polymer and a pH insensitive polymer, and being configured for gastric retention for an extended period of time while maintaining its structural integrity and to release said active or diagnostic agent into the gastric environment of the subject over said period, wherein said release occurs independently of any degradation of the material Aspect 2. The device according to aspect 1 wherein the extended gastric retention is at least six hours.

Aspect 3. The device according to aspect 1 or aspect 2 wherein the pH insensitive polymer is a non-ionic cellulose ester.

Aspect 4. The device according to aspect 1, wherein the enteric polymer comprises a polymethacrylate-based copolymer.

Aspect 5. The device according to aspect 1, wherein the enteric polymer comprises a hydroxypropylmethylcellulose acetate succinate (HPMCAS).

Aspect 6. The device according to aspect 1, wherein the enteric polymer comprises at least one of HPMCAS-HG, and HPMCAS-MG or HPLCAS LG.

Aspect 7. The device according to aspect 6, wherein the enteric polymer comprises HPMCAS-HG and HPMCAS-MG in a ratio of about 10:1 to about 1:1, or a ratio of about 1:1, about 7:3, about 8:2, or about 10:1.

Aspect 8. The device according to aspect 5, wherein the enteric polymer comprises about 80% HPMCAS.

Aspect 9. The device according to any one of the preceding aspects wherein the material comprising the pH insensitive polymer is present as at least a partial coating on a surface of the enteric polymer.

Aspect 10. The device according aspect 9 wherein at least 50% or at least 60% or at least 70% or at least 80% or at least 90% or at least 95% or at least 97% or at least 99% of a surface area of a portion of the device comprising the material is coated by the pH insensitive polymer.

Aspect 11. The device according to aspect 9, wherein the pH insensitive polymer is cellulose acetate.

Aspect 12. The device according to aspect 11, wherein the cellulose acetate is present in an amount of about 30 to about 99% by weight of the solids in said coating.

Aspect 13. The device according to aspect 9, wherein the coating further comprises a second enteric polymer.

Aspect 14. The device according to any one of aspects 11-13, wherein the first enteric polymer is hydroxypropylmethylcellulose (HPMC-AS), polyethylene glycol (PEG), or both.

Aspect 15. The device according to aspect 14, wherein the HPMC-AS is present in the amount of about 30 to about 70% by weight of the solids in said coating.

Aspect 16. The device according to aspect 14, or aspect 15, wherein the PEG is present in the amount of about 0.5 to about 3% by weight of the solids in said coating.

Aspect 17. The device according to any one of the preceding aspect, wherein the material further comprises a plasticizer.

Aspect 18. The device according to aspect 17, wherein the plasticizer is triacetin, polyethylene glycol (PEG), dibutyl sebacate (DBS), or any combination thereof.

Aspect 19. The device according to aspect 18, wherein the plasticizer comprises both triacetin and polyethylene glycol that are present relative to each other in a ratio of about 0.3:1 to 1:0.3.

Aspect 20. The device according to aspect 17, wherein the ratio of enteric polymer to plasticizer is from about 3:1 to about 12:1 or about 6:1 to about 12:1.

Aspect 21. The device according to aspect 18, wherein the material forming the device comprises about 10 parts of HPMC-AS, from 0 to about 1 part triacetin, from 0 to about 1 part PEG, and from 0.5 to about 1.5 part DBS; or, about 10 parts of HPMC-AS, about 0.3 to about 0.6 parts triacetin, from 0.3 to about 1 part DBS and about 0.2 to about 1 parts PEG or about 0.8 to about 1.2 parts triacetin; or, about 10 parts of HPMC-AS and about 0.9 to about 1.5 parts PEG; or, about 10 parts of HPMC-AS and about 0.8 to about 1.2 parts DBS.

Aspect 22. The device according to claim 18, wherein the material forming the device comprises about 10 parts of HPMC-AS and about 0.3 to about 1 parts DBS and 0.2 to about 1 parts of PEG.

Aspect 23. The device according to any one of the preceding aspects, wherein the devices comprises one or more predefined apertures through which the agent is released into the gastric fluid or small intestine.

Aspect 24. The device according to any one of the preceding aspects, wherein administration of the device exposes at least a portion of the agent to the subject's gastric fluid or small intestine such that the device releases the agent through one or more predefined apertures into said fluid or small intestine.

Aspect 25. The device according to any one of the preceding aspects, wherein the device releases the agent into said fluid or small intestine for a period of at least or about eight hours.

Aspect 26. The device according to any one of the preceding aspects, wherein the device releases the agent into said fluid or small intestine for a period of at least or about 12 hours.

Aspect 27. The device according to any one of the preceding aspects, wherein the device releases the agent into said fluid or small intestine for a period of at least or about 18 hours.

Aspect 28. The device according to any one of the preceding aspects, wherein the device releases the agent into said fluid or small intestine for a period of at least or about 24 hours.

Aspect 29. The device according to any one of the preceding aspects, wherein the device releases the agent into said fluid or small intestine for a period of at least or about 48 hours.

Aspect 30. The device according to any one of the preceding aspects, wherein the device releases the agent into said fluid or small intestine for at least or about 72 hours.

Aspect 31. The device according to any one of the preceding aspects, wherein the device releases the agent into said fluid or small intestine for at least or about seven days.

Aspect 32. The device according to any one of the preceding aspects, wherein said material maintains its structural integrity under an applied force of about 150 to about 500 gf following exposure of the device for at least 24 hours to a fluid at pH 2.

Aspect 33. The device according to any one of the preceding aspects, wherein the material swells by no more than about 10% as a result of exposure of the device for at least 24 hours to a fluid at pH 2.

Aspect 34. The device according to any one of the preceding aspects, wherein the material possesses a deformation modulus of about 75 to about 500 gf/mm following exposure of the material for at least 24 hours to a fluid at pH 2.

Aspect 35. The device according to any one of the preceding aspects, wherein the material is shaped, sized, or both shaped and sized to resist passage through the subject's pylorus prior to release of at least 50% of the agent that is present in the device prior to administration to the patient.

Aspect 36. The device according to any one of the preceding aspects, wherein the material is shaped, sized, or both shaped and sized to resist passage through the subject's pylorus prior to release of at least 70% of the agent that is present in the device prior to administration to the patient.

Aspect 37. The device according to any one of the preceding aspects, wherein the material is shaped, sized, or both shaped and sized to resist passage through the subject's pylorus prior to release of at least 90% of the agent that is present in the device prior to administration to the patient.

Aspect 38. The device according to any one of the preceding aspects having a compressed configuration when housed within a capsule prior to oral administration, and having an expanded configuration following dissolution of the capsule in the subject's stomach following oral administration, the expanded configuration being sized so as to prevent passage of the device through the subject's pylorus.

Aspect 39. The device according to any one of the preceding aspects wherein the active or diagnostic agent is at least partially housed on or within the material.

Aspect 40. The device according to aspect 39 wherein the material is configured to release the active or diagnostic agent in a controlled manner.

Aspect 41. The device according to aspect 39 wherein the material includes one or more predefined apertures through which the active or diagnostic agent is released into the gastric fluid or into the small intestine of the subject.

Aspect 42. A method for providing extended release of an agent within a subject comprising orally administering to the subject a device according to any one of the preceding aspects. A device for delivering an active or diagnostic agent to a human subject's gastric environment via oral administration and being configured for gastric retention for an extended period of time, said device comprising a material that comprises an enteric polymer and a pH insensitive polymer, wherein the material maintains structural integrity as measured using a pharmacopoeia dissolution apparatus II, 400 mL, at 37° C., 100 RPM, containing HCl 0.1N+Xanthan 0.125 g/L (pH 2), and shows degradability as measured using a pharmacopoeia dissolution apparatus II, 400 mL, at 37° C., 100 RPM, containing 6 g/L sodium phosphate (pH 6.8).

Aspect 43. A component or device configured for gastric retention over an extended period of time following oral administration to a human subject comprising a material that is characterized by structural integrity or dimensional integrity in the stomach or simulated gastric conditions, and degradability in the intestine or simulated intestinal conditions.

Aspect 44. The component or device according to aspect 43 wherein the material comprises an enteric polymer and a pH insensitive polymer.

Aspect 45. The component or device according to aspect 44 wherein the pH insensitive polymer is present on at least 50% or at least 60% or at least 70% or at least 80% or at least 90% or at least 95% or at least 97% or at least 99% of the total surface area of a portion of the device comprising the material is coated by the pH insensitive polymer.

Aspect 46. The component or device according to aspect 44 wherein the pH insensitive polymer is present as at least a partial coating on a surface of the enteric polymer.

Aspect 47. The component or device according to aspect 46, wherein the coating further comprises a second enteric polymer.

Aspect 48. The component or device according to any one of aspects 44-47, wherein the enteric polymer is HPMCAS-HG, HPMCAS-MG, or HPMCAS-LG Aspect 49. The component or device according to any one of aspects 44-48, wherein pH insensitive polymer is a non-ionic cellulose ester.

Aspect 50. The component or device according to any one of aspects 44-48, wherein pH insensitive polymer is a non-ionic cellulose acetate.

Aspect 51. The component or device according to any one of aspects 43-50 wherein the structural integrity of the component or device is at least 60%, at least 80%, or about 100% after 24 hours of the value measured at t=0, as measured using a pharmacopeia dissolution apparatus II, 400 mL, at 37° C., 100 RPM, containing HCl 0.1N+Xanthan 0.125 g/L (pH 2).

Aspect 52. The component or device according to any one of aspects 43-51, wherein change in width of the component or device relative to the width at t=0 is less than 10%, less than 5%, less than 2%, or about 0% as measured after 24 hours in a pharmacopeia dissolution apparatus II, 400 mL, at 37° C., 100 RPM, containing HCl 0.1N+Xanthan 0.125 g/L (pH 2).

Aspect 53. The component or device according to any one of aspects 43-52, wherein the component retains less than 60%, less than 40%, less than 20%, or about 0% of the original rigidity (t=0) of the component or device as measured after 24 hours in a pharmacopeia dissolution apparatus II, 400 mL, at 37° C., 100 RPM, containing 6 g/L sodium phosphate (pH 6.8).

Aspect 54. The component or device according to any one of aspects 43-53, wherein the component or device retains less than 65% of the original rigidity (t=0) of the component or device, as measured after 8 hours in a pharmacopoeia dissolution apparatus II, 400 mL, at 37° C., 100 RPM, containing 6 g/L sodium phosphate (pH 6.8).

Aspect 55. The component or device according to any one of aspects 51-54, wherein the pH insensitive polymer is a non-ionic cellulose ester.

Aspect 56. The component or device according to aspect 55, wherein the non-ionic cellulose ester is cellulose acetate.

Aspect 57. Use of a material comprising a pH insensitive polymer and pH sensitive polymer in the formation of a device or component configured for gastric retention, wherein said material is characterized by degradability in the intestine or under simulated intestinal conditions, and structural integrity in the gastric environment or simulated gastric conditions.

Aspect 58. A method of maintaining rigidity or structural integrity of a component of a device for delivering an active or diagnostic agent over an extended period of time in a human subject's gastric environment while maintaining degradability in a human subject's intestinal environment comprising forming the component or device using a material comprising an enteric polymer and a pH insensitive polymer.

Aspect 59. Use of a material comprising an enteric polymer and a pH insensitive polymer in the formation of a device or component configured for oral administration and for gastric retention while maintaining its structural integrity and dimensional integrity in the stomach and being characterized by degradability in the intestine.

Aspect 60. The use according to aspect 59 wherein the wherein structural integrity of the material is at least 60%, at least 80%, or about 100% of the original value as measured by the rigidity [1] test after 24 hours.

Aspect 61. The use according to aspect 59 wherein the dimensional integrity of the material is characterized by a less than 10%, less than 5%, less than 2%, or about 0% change in width as measured after 24 hr in a pharmacopeia dissolution apparatus II, 400 mL, at 37° C., 100 RPM, containing HCl 0.1N+Xanthan 0.125 g/L (pH 2), relative to the original width of the device or component.

Aspect 62. The use according to aspect 59 wherein the degradability of the material is characterized by a measured rigidity that is less than 60%, less than 40%, less than 20%, or about 0% at 24 hours of a rigidity value measured at t=0, as measured using the rigidity [2] test.

Aspect 63. The use according aspect 59 wherein the degradability of the material is characterized by a measured rigidity that is less than 65% at 8 hours of a rigidity value measured at t=0, as measured by the rigidity [2] test at 8 hrs.

Aspect 64. The use according aspect 59, wherein the material swells by no more than about 10% as a result of exposure of the device for at least 24 hours to a fluid at pH 2.

Aspect 65. The use according aspect 59, wherein the material possesses a deformation modulus of about 75 to about 500 gf-mm following exposure of the device for at least 24 hours to a fluid at pH 2.

Aspect 66. The use according aspect 59, wherein the device or component releases a therapeutic or diagnostic agent into the gastric environment occurs that independently of dissolution or degradation of the material.

Aspect 67. The use according aspect 66, wherein release of the agent into the subject's gastric environment is substantially zero order.

Aspect 68. The use according aspect 59, wherein the enteric polymer comprises a polymethacrylate-based copolymer.

Aspect 69. The use according aspect 59, wherein the enteric polymer comprises hydroxypropylmethylcellulose acetate succinate (HPMC-AS).

Aspect 70. The use according aspect 59, wherein the enteric polymer comprises one or both of HPMCAS-HG and HPMCAS-MG.

Aspect 71. The use according aspect 59, wherein the enteric polymer comprises both HPMCAS-HG and HPMCAS-MG in a ratio of about 10:1 to about 1:2.

Aspect 72. The use according aspect 59, wherein the enteric polymer comprises both HPMCAS-HG and HPMCAS-MG in a ratio of about 1:2, about 7:3, about 8:2, or about 10:1.

Aspect 73. The use according aspect 59, wherein the enteric polymer is at least about 80% HPMCAS.

Aspect 74. The use according to aspect 73, wherein the pH insensitive polymer is cellulose acetate that present as a coating on a surface of the HPMC-AS.

Aspect 75. The use according to aspect 74, wherein the cellulose acetate is present in the amount of about 30 to about 99% by weight of the solids in said coating.

Aspect 76. The use according to aspect 74 or aspect 75, wherein the coating further comprises hydroxypropylmethylcellulose (HPMC-AS), polyethylene glycol (PEG), or both.

Aspect 77. The use according to aspect 76, wherein the HPMC-AS is present in the amount of about 30 to about 70% by weight of the solids in said coating.

Aspect 78. The use according to aspect 76, wherein the PEG is present in the amount of about 1 to about 3% by weight of the solids in said coating.

Aspect 79. The use according to any one of aspects 59-78, wherein the material used in the formation of the device further comprises a plasticizer.

Aspect 80. The use according to aspect 79, wherein the plasticizer is triacetin, polyethylene glycol (PEG), dibutyl sebacate (DBS), or any combination thereof.

Aspect 81. The use according to aspect 80, wherein the plasticizer comprises both triacetin and polyethylene glycol that are present relative to each other in a ratio of about 0.3:1 to 1:0.3.

Aspect 82. The use according to any one of aspects 79-81, wherein the ratio of enteric polymer:plasticizer is from about 4:1 to about 12:1.

Aspect 83. The use according to any one of aspects 79-81, wherein the ratio of enteric polymer: plasticizer is about 6:1 to about 12:1.

Aspect 84. The use according to any one of aspects 59-83, wherein the material used in the formation of the device comprises about 10 parts of HPMC-AS, from 0 to about 1 part triacetin, from 0 to about 1 part PEG, and from 0 to about 1 part DBS.

Aspect 85. The use according to any one of aspects 59-83, wherein the material used in the formation of the device comprises about 10 parts of HPMC-AS, about 0.4 to about 0.5 parts triacetin, and about 0.7 to about 0.9 parts PEG.

Aspect 86. The use according to any one of aspects 59-83, wherein the material used in the formation of the device comprises about 10 parts of HPMC-AS and about 0.8 to about 1.2 parts triacetin.

Aspect 87. The use according to any one of aspects 59-83, wherein the material used in the formation of the device comprises about 10 parts of HPMC-AS and about 0.9 to about 1.5 parts PEG.

Aspect 88. The use according to any one of aspects 59-83, wherein the material used in the formation of the device comprises about 10 parts of HPMC-AS and about 0.8 to about 1.2 parts DBS.

Aspect 89. A method for making a device for providing extended release of an active or diagnostic agent in the gastric environment of a human subject via oral administration comprising:

forming the device using a material that comprises an enteric polymer and a pH insensitive polymer, the device being configured for gastric retention while maintaining its structural integrity while in the gastric environment; and, loading the device with the agent such that the agent is released over a period of at least six hours independently of any degradation of the material in the gastric environment.

Aspect 90. The method according to aspect 89, wherein the material is shaped by injection molding the enteric polymer.

Aspect 91. The method according to aspect 89 or aspect 90, wherein the enteric polymer comprises a cellulose-based polymer.

Aspect 92. The method according to any one of aspects 89-91, wherein the enteric polymer comprises hydroxypropylmethylcellulose acetate succinate (HPMCAS).

Aspect 93. The method according to aspect 92, wherein the enteric polymer comprises about 90% or at least 90% HPMCAS.

Aspect 94. The method according to any one of aspects 89-93, wherein the enteric polymer comprises one or both of HPMCAS-HG and HPMCAS-MG.

Aspect 95. The method according to any one of aspects 89-94, wherein the enteric polymer comprises a polymethacrylate-based copolymer.

Aspect 96. The method according to any one of aspects 89-95, wherein the material further comprises a plasticizer.

Aspect 97. The method according to any one of aspects 89-96, wherein a surface of the enteric polymer is at least partially coated with the pH insensitive polymer.

Aspect 98. The method according to any one of aspects 89-97, wherein the pH insensitive polymer is a non-ionic cellulose ester.

Aspect 99. The method according to aspect 97 or aspect 98, wherein the coating further comprises hydroxypropylmethylcellulose (HPMC-AS), polyethylene glycol (PEG), or both.

Aspect 100. The method according to aspect 99, wherein HPMC-AS is present in an amount of about 30 to about 70% by weight of the solids in said coating.

Aspect 101. The method according to aspect 99 or aspect 100, wherein PEG is present in an amount of about 1 to about 3% by weight of the solids in said coating.

Aspect 102. The method according to any one of aspects 97-101, wherein the pH insensitive polymer is cellulose acetate that is present in an amount of about 30 to about 99% by weight of the solids in said coating.

Aspect 103. A device for providing extended release of a drug within a subject comprising:

a carrier portion for transporting said drug to the stomach of the subject via oral administration, the carrier portion comprising at least two subparts, each being formed from a material that resists degradation within the stomach for at least six hours, and, the carrier portion being configured to resist passage through the subject's pylorus absent physical separation of the subparts from each other, the drug being present in said carrier portion in the form of a depot structure positioned within at least one of said subparts of the carrier portion, wherein the subparts of the carrier portion are configured to separate when at least 50% of the depot structure is dissolved due to release of the drug into the subject's stomach;

and, a coating on the outer surface of the carrier portion, wherein delivery of the device to the subject's stomach exposes at least a portion of the depot structure to the subject's gastric fluid such that the depot structure releases the drug into said fluids for a period of at least or about six hours.

Aspect 104. The device according to aspect 103, wherein the subparts of the carrier portion are configured to separate when at least 70% of the depot structure is dissolved due to release of the drug into the subject's stomach.

Aspect 105. The device according to aspect 103, wherein the subparts of the carrier portion are configured to separate when at least 80% of the depot structure is dissolved due to release of the drug into the subject's stomach.

Aspect 106. The device according to aspect 103, wherein the subparts of the carrier portion are configured to separate when at least 90% of the depot structure is dissolved due to release of the drug into the subject's stomach.

Aspect 107. The device according to aspect 103, having a compressed configuration when housed within a capsule prior to oral delivery, and having an expanded configuration following dissolution of the capsule in the subject's stomach following oral delivery, the expanded configuration being sized so at to prevent passage of the device through the subject's pylorus.

Aspect 108. The device according to aspect 107, wherein the subparts include a hinge piece, and first and second arm pieces that are both joined to the hinge piece, and wherein the first and second arm pieces are proximate to each other in the compressed configuration of the device, and are spaced apart from each other in the expanded configuration of the device.

Aspect 109. The device according to aspect 108, wherein the hinge piece is configured to separate from the first and second arm pieces when at least 50% of the depot structure is dissolved due to release of the drug into the subject's stomach.

Aspect 110. A method for providing extended release of a drug within a subject comprising orally administering to the subject a device according to any one of aspects 103-109.

Aspect 111. The method according to aspect 110, wherein the device is housed within a capsule prior to the oral administration, and wherein the capsule dissolves within the subject's stomach following delivery of the device thereto.

Aspect 112. A method for making a device for providing extended release of a drug within a subject comprising:

forming a pellet by hot melt extrusion, the pellet comprising a material that resists degradation within a subject's stomach for at least six hours;

forming by injection molding at least two subparts of a carrier portion of the device;

coating a surface of at least one of the subparts of the carrier portion of the device;

loading one or more of the subparts with a drug depot structure; and, assembling the subparts of the carrier portion in order to form the device

EXAMPLES

The following examples are set forth so as to provide those of ordinary skill in the art with a complete disclosure and description of how the devices claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for.

Example 1a

Figure 4A:
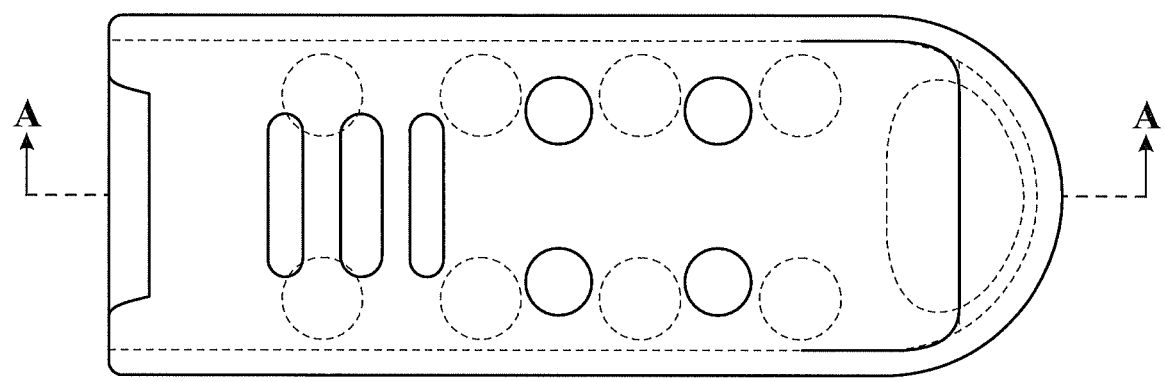
FIGS. 4A, 4B, and 4C depict views of a component formed using inventive materials that was tested for structural integrity and degradability.
Figure 4A:
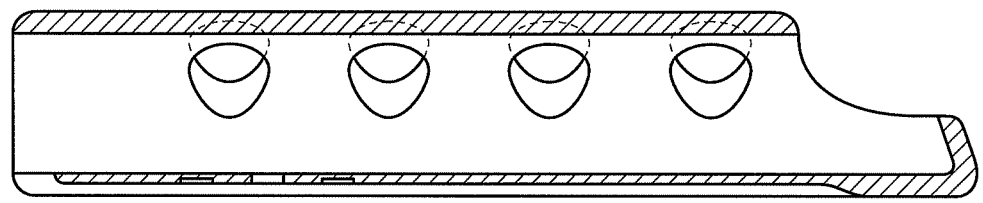
Figure 4A:
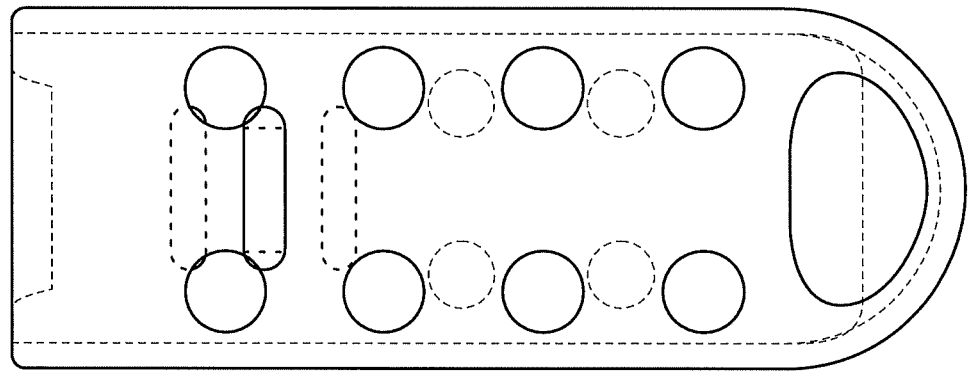
Figure 4B:
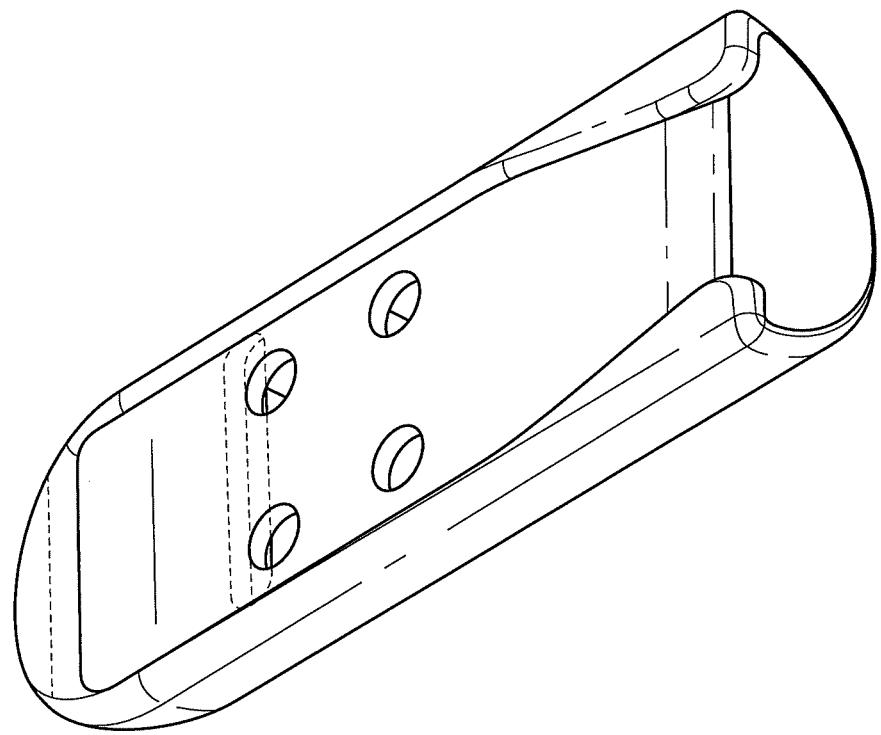
Figure 4C:
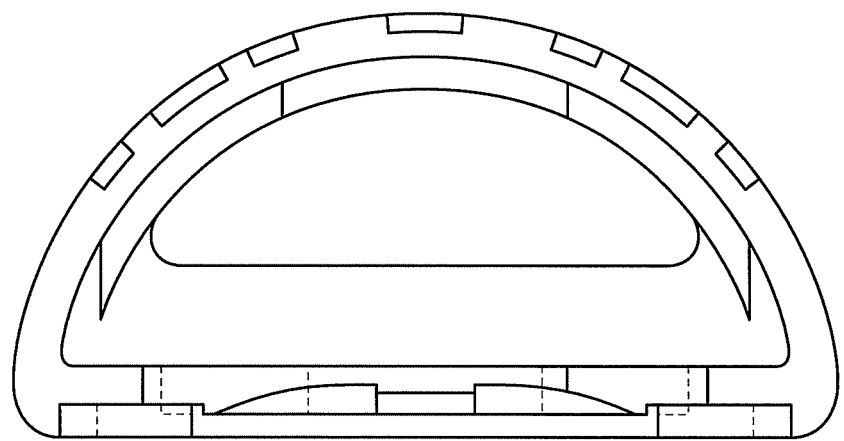

Preparation of Injection Molded Material for Use in Forming Gastric Retentive Devices Holt melt extrudant samples 2-12, and comparative extrudant 1, were prepared using the parameters listed below in Table 1 and by the same method as disclosed in WO 2015/187746, Example 1A and 1B, which is incorporated herein by reference. Extrudants were placed in an injection molding machine to obtain molded objects, for example, a Type A component as depicted in FIG. 4A-4C. Each molded object, for example a Type A component, was then either coated or left uncoated.

TABLE 1

| Sample No. | Polymers | Plasticizers | Components ratio | Polymer:Plasticizer ratio | Pre-Mixing time (min, RPM) | Hot melt flow rate 1 kg/hr | HME temp 1 [° C.] | HME temp 2 [° C.] | Milled pellets diameter |
|---|---|---|---|---|---|---|---|---|---|
| 1 | Cellulose acetate | Triacetin | 4:1 | 4 | 2 min, 500 RPM | 1.8 | 180 | 200 | 1.5 mm |
| 2 | HMPCAS HG | Triacetin | 10:0.83 | 12 | 2 min, 500 RPM | 1.8 | 130 | 150 | 1.5 mm |

TABLE 1-continued

| Sample No. | Polymers | Plasticizers | Components ratio | Polymer:Plasticizer ratio | Pre-Mixing time (min, RPM) | Hot melt flow rate 1 kg/hr | HME temp 1 [° C.] | HME temp 2 [° C.] | Milled pellets diameter |
|---|---|---|---|---|---|---|---|---|---|
| 3 | HMPCAS HG | PEG 3350 | 10:1 | 10 | 2 min, 500 RPM | 1.8 | 130 | 150 | 1.5 mm |
| 4 | HMPCAS HG | DBS | 10:0.83 | 12 | 2 min, 500 RPM | 1.8 | 130 | 150 | 1.5 mm |
| 5 | HMPCAS HG, AG | PEG 3350 | 7:3:1.4 | 7.14 | 2 min, 500 RPM | 1.8 | 130 | 150 | 1.5 mm |
| 6 | HMPCAS HG, MG | Triacetin, PEG 3350 | 5:5:0.5:0.9 | 0.89 | 2 min, 500 RPM | 1.8 | 130 | 150 | 1.5 mm |
| 7 | HMPCAS HG, MG | Triacetin, PEG 3350 | 7:3:0.45:0.75 | 8.3 | 2 min, 500 RPM | 1.8 | 130 | 150 | 1.5 mm |
| 8 | HMPCAS HG, MG | Triacetin, PEG 3350 | 8:2:0.4:0.77 | 8.5 | 2 min, 500 RPM | 1.8 | 130 | 150 | 1.5 mm |
| 9 | HMPCAS HG, MG | DBS | 8:2:1 | 10 | 2 min, 500 RPM | 1.8 | 130 | 150 | 1.5 mm |
| 10 | HMPCAS HG, MG | DBS | 8:2:1.2 | 8.3 | 2 min, 500 RPM | 1.8 | 130 | 150 | 1.5 mm |
| 11 | HMPCAS HG, MG | DBS, PEG 3350 | 8:2:0.7:0.3 | 8.3 | 2 min, 500 RPM | 1.8 | 130 | 150 | 1.5 mm |
| 12 | HMPCAS HG | DBS | 10:1 | 8.3 | 2 min, 500 RPM | 1.8 | 130 | 150 | 1.5 mm |

With reference to sample numbers 6-8, the materials that were loaded into the hot melt extruder (HME machine) were prepared by the following sequential steps:

a. The polymer was premixed with the dry plasticizer in DIOSNA mixer [6 L] for 3 min, 500 RPM.

b. The HME machine was pre-heated to the defined temperature.

c. The mixture was fed into the HME machine (e.g., by a gravimetric feeder at 1.8 kg/hr rate).

d. With synchronization to feeder rate the liquid plasticizer was added with peristaltic pump directly into the HME.

e. The HME snail speed was set to 150 RPM.

f. As the melted material was drawn from the HME machine it was forwarded as strands onto a conveyor belt and cooled. Once cooled, the strand was chopped by a chopping machine to particles of about 1.5-2 mm size.

g. After chopping, the material was dried under vacuum at 50° C. for 5 hr to enable water evaporation (loss on drying recorded at below 1%) to produce HME for next stage.

Preparation of parts via injection molding using HME. The relevant mold configuration was placed in a suitable injection molding machine (Wittman EcoPower 55 Ton Injection Molding Machine). The hot melt extrudants were molded into parts of the device, for example, using the parameters listed in Table 2, below.

TABLE 2

| Samples No. | Polymer:Plasticizer ratio | barrel temp [C. °] | nozzle temp [C. °] | mold temperature | hold pressure [Bar] | injection speed | cycle time [sec] |
|---|---|---|---|---|---|---|---|
| 7 | 8.3 | 150-170 | 190-210 | 60 | 1100 | 90 | 15 |
| 8 | 8.5 | 150-170 | 190-210 | 60 | 1100 | 150 | 15 |

For example, sample 7 was inserted into the injection molding machine. Screw temperature was set at 150-170° C., nozzle temperature to 200° C. and mold temperature was set to 60° C. The injection molding cycle was 15 seconds.

Coating of the molded parts. Samples of the molded objects from extrudate samples 1-12 as described in Table 1 were coated in a lab scale VECTOR coater machine with different coating compositions. The coating conditions were at 20° C., spray of 1200 mbar, pump speed 10 RPM, pan speed of 20 RPM. The coating obtaining was 1 to 5% weight gain. The coating compositions are described in Table 3, below.

TABLE 3

| Coat | coating solvent | % solids | % coat (weight gain %) | cellulose acetate % of solids | HPMCAS MG % of solids | PEG 3350 % of solids |
|---|---|---|---|---|---|---|
| 1 | acetone:water 95:5 | 3.10% | 3.50% | 99 | 0 | 1 |
| 2 | acetone:water 95:5 | 3.10% | 5.00% | 69 | 30 | 1 |
| 3 | acetone:water 95:5 | 3.10% | 3.50% | 69 | 30 | 1 |
| 4 | acetone:water 95:5 | 3.10% | 2.00% | 69 | 30 | 1 |
| 5 | acetone:water 95:5 | 3.10% | 3.50% | 49.5 | 49.5 | 1 |
| 6 | acetone:water 95:5 | 3.10% | 3.50% | 30 | 69 | 1 |
| 7 | acetone:water 95:5 | 3.10% | 3.50% | 0 | 99 | 1 |

A stepwise summary of an exemplary coating process is as follows:
1. Weighed and dissolved 0.25 gr PEG3350 in 10 ml water
2. Weighed 190 ml acetone and added PEG solution while mixing
3. Weighed 17.2 gr cellulose acetate and added to solution while mixing
4. Weighed 7.8 gr HPMCAS MG and added to solution while mixing
5. Added 600 cc of acetone:water 95:5 v/v and mixed well.

In vitro testing of coated parts. The durability of the test articles bearing different coatings was measured after exposure to a medium at pH 2 and pH6.8. Test articles were placed in a rotating apparatus (VanKel Rotating Bottle apparatus, Varian, Inc.) to test durability under simulated gastric and intestinal conditions. The molded object was placed in a 500 mL dissolution chamber bottle with 400 mL HCl 0.01N (pH 2) at 37° C. The dissolution chamber was rotated at 20 RPM. At 0, 2, 4, 8, and 24 hr time points, the test article was extracted and subjected to the following tests:
  a. Plain deformation: visual deformation, change in structure length, loss of detailed structures, change in weight.
  b. Deformation under mechanical force of 180 g up to 350 g for 5 sec.

In the second step, the test medium was a pH 6.8 buffer phosphate and the aforementioned steps (a. and b.) were carried out at 2, 6, and 24 hr time points.

Figure 2:
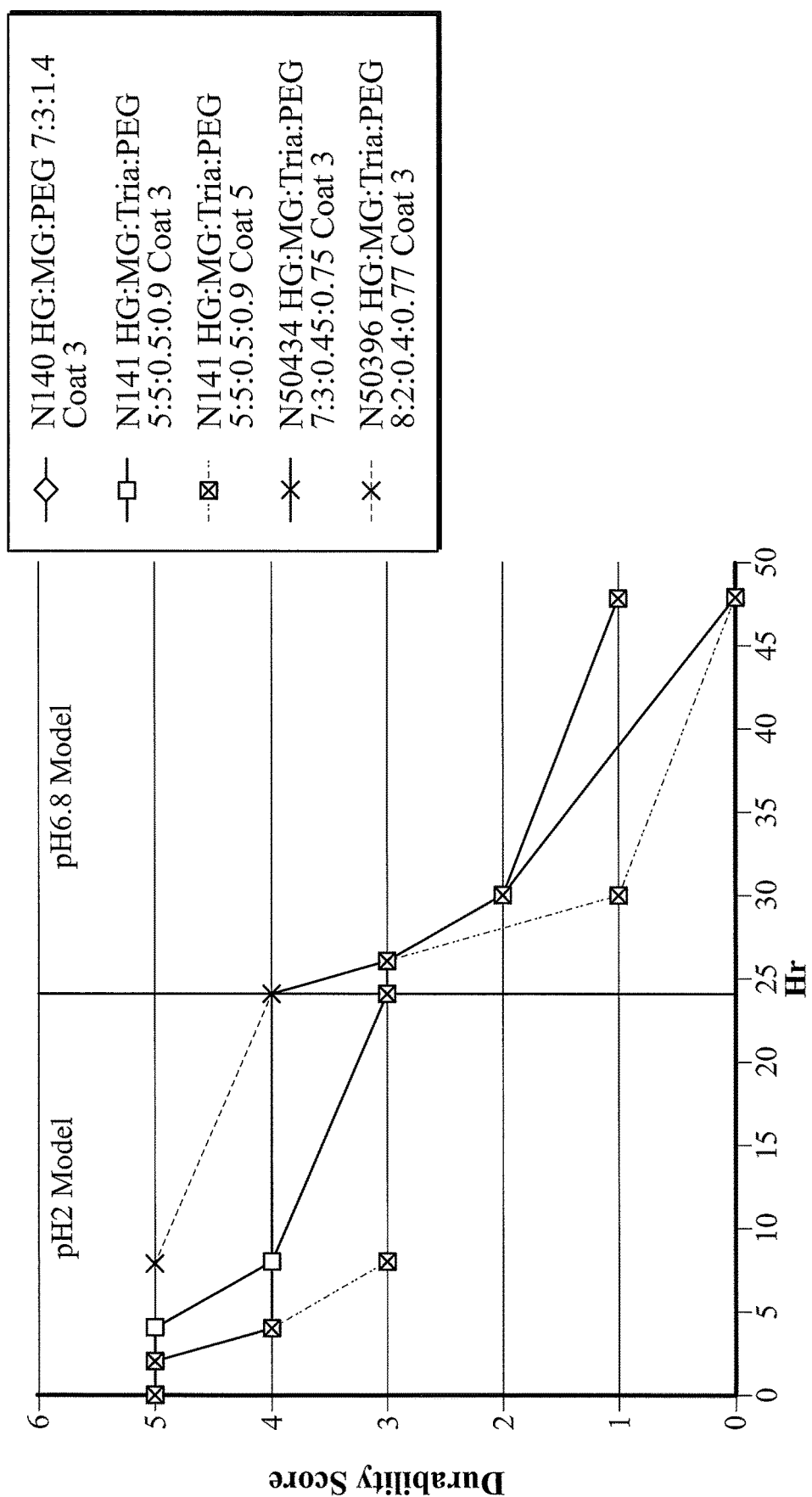
FIG. 2 is a graphical depiction of the durability scores over time of polymer compositions bearing various coating compositions.

In Table 4a, below, the durability score, assessed by touch and sight by a skilled artisan, was assigned as follows: Five=high durability-low degradability (approximating the starting condition) and zero=low durability-high degradability (e.g. no material remained).

coating composition. FIG. 2 is a graphical depiction of the durability scores over time of certain of the above-described polymer compositions bearing various coating compositions.

Example 1b

Preparation of Injection Molded Material for Forming Gastric Retentive Devices

Additional type A components having different material compositions and coating compositions were made in the same manner as described in Example 1a. An assessment was conducted regarding the effect of various coating compositions (uncoated, coat 3, coat 5) on durability. Results are shown in Tables 8-10, below. Structural integrity of tested samples was evaluated by degree of deformation after 24 hr exposure to pH 2 medium ("rigidity I": measuring % change in width and visual inspection of details lost), and by degree of erosion in pH 6.8 ("rigidity II": approximate % stiffness retained). Samples were given a durability score of 0 to 5 in each pH, where a score of 5 corresponded to high durability, and a score of 0 corresponded to high degradability. In addition, a "rigidity difference" score was calculated by subtracting the rigidity score at 6.8 rigidity from the rigidity score at pH 2. The objective of the test was to determine the conditions under which it was possible to obtain the highest possible structural integrity at pH 2 and the lowest possible durability at pH 6.8, mimicking the gastric and intestinal milieu, respectively. A given material preferably meets the following durability test criteria: "rigidity I"≥3, "rigidity II"≤2, "rigidity difference"≥2. Table 4b indicates whether these criteria were met ("yes" or "no").

Rigidity measurement is defined as follows: applied X force of orientation Y causing deformation of Z. If Z is lower than K, then the rigidity is score 5.

TABLE 4a

| | Mold | | Brittleness | Durability degradability score 5 = high durability 0 - high degradability | | | | | | | Description of |
|---|---|---|---|---|---|---|---|---|---|---|---|
| Sample | | Coat Type | % breaks during | | pH 2 | | | | pH 6.8 | | Visually Apparent |
| No. | Composition | (see Table 3) | Mold Config. | assembly | 0 | 2 | 4 | 8 | 24 | 26 | 30 | 48 | Deformation |
| 1 | N153 CA:Tria 4:1 | No | type A | | 5 | 5 | 5 | 5 | 5 | 5 | 5 | 4 | |
| 2a | N103 HG:Tria 12:1 | No | type A | 30% | 5 | 4 | 3 | 2 | 2 | 2 | 1 | 0 | high shrinking (in pH 2) |
| 2b | N103 HG:Tria 12:1 | coat 3 | type A | 10% | 5 | 4 | 4 | 3 | 3 | 3 | 2 | 1 | minor shrinking (in pH 2) |
| 3a | N106 HG:PEG 10:1 | No | type A | 30% | 5 | 4 | 3 | 3 | 2 | 2 | 1 | 0 | high swelling (in pH 2) |
| 3b | N106 HG:PEG 10:1 | coat 3 | type A | 10% | 5 | 4 | 4 | 3 | 3 | 3 | 2 | 0 | minor swelling |
| 4a | N107 HG:DBS 12:1 | No | type A | 40% | 5 | 4 | 4 | 3 | 3 | 2 | 1 | 0 | minor swelling |
| 4b | N107 HG:DBS 12:1 | coat 3 | type A | 10% | 5 | 5 | 4 | 4 | 4 | 3 | 2 | 1 | minor |
| 5 | N140 HG:MG:PEG 7:3:1.4 | coat 3 | type A assembled | 10% | 5 | 5 | 4 | 4 | 3 | 3 | 2 | 0 | medium swelling (in pH 2) |
| 6a | N141 HG:MG:Tria:PEG 5:5:0.5:0.9 | coat 3 | type A assembled | 10% | 5 | 5 | 4 | 4 | 3 | 3 | 2 | 1 | minor |
| 6b | N141 HG:MG:Tria:PEG 5:5:0.5:0.9 | coat 5 | type A assembled | 10% | 5 | 5 | 4 | 3 | 3 | 3 | 1 | 0 | minor |
| 7 | K-50434 HG:MG:Tria:PEG 7:3:0.45:0.75 | coat 3 | type A assembled | 10% | 5 | 5 | 5 | 4 | 3 | 3 | 2 | 0 | minor |
| 8 | K-50396 HG:MG:Tria:PEG 8:2:0.4:0.77 | coat 3 | type A assembled | 10% | 5 | 5 | 5 | 5 | 4 | 3 | 2 | 1 | minor swelling |

FIG. 1 is a graphical depiction of the durability scores over time of certain of the above-described polymer compositions, with or without plasticizer, and with or without a As noted above, the objective was to identify materials possessing the highest possible structural integrity in pH 2, and the lowed durability in pH 6.8. For example, a given material preferably meets all structural integrity test criteria, i.e., rigidity I≥3, rigidity II≤2, and rigidity difference≥2, and more preferably a score of 3, 4, or 5.

Example 2

Deformation of Objects Prepared by Hot Melt Extrusion

Sample objects in the form of tubes were formed by hot melt extrusion to have a diameter of 2 mm and length of 3 cm following the hot melt extrusion manufacturing parameters as described in Table 1 (Example 1a, supra). Five different compositions, shown below in Table 5, were tested in the form of tube samples.

TABLE 5

| Batch Number | HG | MG | Triacetin | PEG | DBS | Ratio of polymer to plasticizer |
|---|---|---|---|---|---|---|
| N-169 | 8 | 2 | 0 | 0 | 1 | 10.0 |
| N-170 | 8 | 2 | 0 | 0 | 1.2 | 8.3 |
| N-171 | 8 | 2 | 0 | 0.3 | 0.7 | 10.0 |
| N-172 | 10 | 0 | 0 | 0 | 1 | 10.0 |
| N-173 | 8 | 2 | 0.45 | 0.75 | 0 | 8.3 |

Each of the tube samples were exposed to simulated gastric conditions: a liquid medium containing 0.1N HCl containing 0.125 g/L xanthan gum at 37° C. for 24 hours in an apparatus that rotated at 20 RPM. After 24 hours, the tube samples were extracted from the apparatus and placed on a three-point bend adaptor in a TEXTUXE analyzer system equipped with a 50 kg load cell. The adaptor was set to descend at a rate of 0.5 mm/s. At a contact force of 10 grams, the system commenced recording the force of deformation, and recording continued until the adaptor descended 1 cm (20 seconds total). For each sample, testing was performed in triplicate. The deformation modulus (force/distance) and maximum force were recorded. Table 6, below, shows the results of these tests for each sample.

TABLE 6

| Batch Number | Deformation Modulus (Δ Force/Δ Distance, Gradient F-T 1:2 g/sec) | Max Force (g) |
|---|---|---|
| N-169 | 347.4 | 477.2 |
| N-170 | 213.7 | 509.9 |
| N-171 | 209.0 | 460.1 |
| N-172 | 126.3 | 326.7 |
| N-173 | 70.3 | 210.3 |

Figure 3:
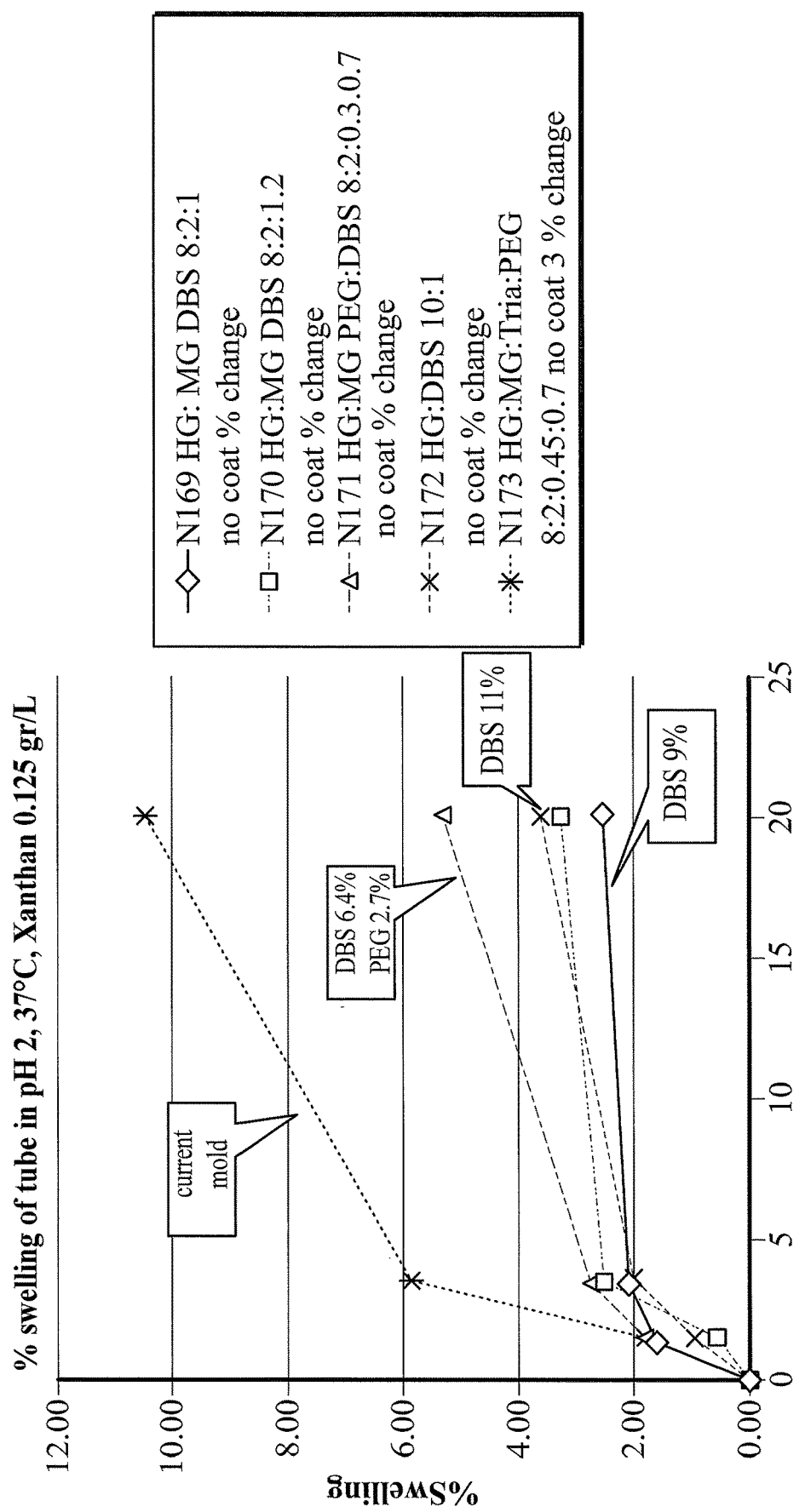
FIG. 3 illustrates the results of an assessment of the degree of swelling of the various sample compositions after exposure to simulated gastric medium after 24 hours.

FIG. 3 illustrates the results of an assessment of the degree of swelling of the various tube samples in the simulated gastric medium.

Example 3

Assessment of Dimensional Integrity and Rigidity

Multiple versions of a component for potential use in a gastric retentive device were prepared as described in Examples 1A and 1B of WO 2015/187746, incorporated herein by reference. Such component may be the carrier portion, for example. The mold configuration that was used to form the components, referred to herein as "type A", was the same as in Example 1a, above. The resulting objects are shown in FIGS. 4A, 4B, and 4C. In brief, the materials used in manufacturing the component were mixed (such as by wet granulation), the resulting mixture was subjected to hot melt extrusion in order to prepare beads that were themselves injected into an injection molding machine to obtain the type A part. The part was left uncoated or was coated with one of coating types 1-7 as described in Table 3 of Example 1a. Table 7, below, lists the specific compositions that were used to prepare individual components, as well as the coating type that was used in connection with each specific composition.

TABLE 7

| Sample No. | Composition | Coat Type | Breaks During Assembly (%) |
|---|---|---|---|
| 1 | CA:Tria 4:1 | no coat | 0 |
| 2 | HG:MG:Tria:PEG 7:3:0.45:0.75 | no coat | 50 |
| 3 | HG:MG:Tria:PEG 7:3:0.45:0.75 | coat 3 | 20 |
| 4 | HG:MG:Tria:PEG 7:3:0.45:0.75 | coat 5 | 20 |
| 5 | HG:MG DBS 8:2:1 | no coat | 20 |
| 6 | HG:MG:DBS 8:2:1 | coat 3 | 10 |
| 7 | HG:MG:DBS 8:2:1 | coat 5 | 10 |
| 8 | HG:MG:DBS:PEG 8:2:0.7:0.3 | no coat | 15 |
| 9 | HG:MG:DBS:PEG 8:2:0.7:0.3 | coat 3 | 5 |
| 10 | HG:MG:DBS:PEG 8:2:0.7:0.3 | coat 5 | 5 |

HG = HPMCAS-HG;
MG = HPMCAS-MG;
LG = HPMCAS-LG;
Tria = Triacetin

Test 1: Dimensional integrity test. In order to assess the ability of a particular component to retain its original dimensions following exposure to simulated gastric conditions, the width of a given component was selected as a relevant parameter and measured both before and after such exposure. Each type A component was placed into a pharmacopoeia dissolution apparatus II, 400 mL, at 37° C., 100 RPM, containing HCl 0.1N+Xanthan 0.125 g/L for 24 hours. At both t=0 and t=24 hours the width (W) of Type A was measured. Percentage change in width was calculated as [Absolute Value$(W_t-W_0)$]/$W_0$×100 wherein $W_t$ is the width at t=24 hours and $W_0$ is the width at t=0. The results for each component are shown in Table 8, below. Any component displaying a change in width of less than 10% is said to meet the requirement for dimensional integrity.

TABLE 8

| | | pH 2 phase - Dimensional Integrity tests (apparatus II, 400 mL, 37°, 100 RPM HCl 0.1N + Xanthan 0.125 g/L) % change in width = [$(W_t - W_0)/W_0$] × 100 | | | |
|---|---|---|---|---|---|
| Composition Tested (Type A mold) | | Width at t = 0 | Width at 24 hr | % change | Meets integrity |
| Batch No. | SampleNo. | (mm) | (mm) | width | criteria? |
| A | 1 | 9.0 | 8.9 | 1.1 | Y |
| B | 2 | 9.0 | 7.95 | 11.7 | N |
| B | 3 | 9.0 | 8.6 | 4.4 | Y |
| B | 4 | 9.0 | 8.4 | 6.7 | Y |
| C | 5 | 9.0 | 6.6 | 26.7 | N |
| C | 6 | 9.0 | 8.8 | 2.2 | Y |
| C | 7 | 9.0 | 8.6 | 4.4 | Y |
| D | 8 | 9.0 | 7.5 | 16.7 | N |
| D | 9 | 9.0 | 8.9 | 1.1 | Y |
| D | 10 | 9.0 | 8.8 | 2.2 | Y |

Figure 5:
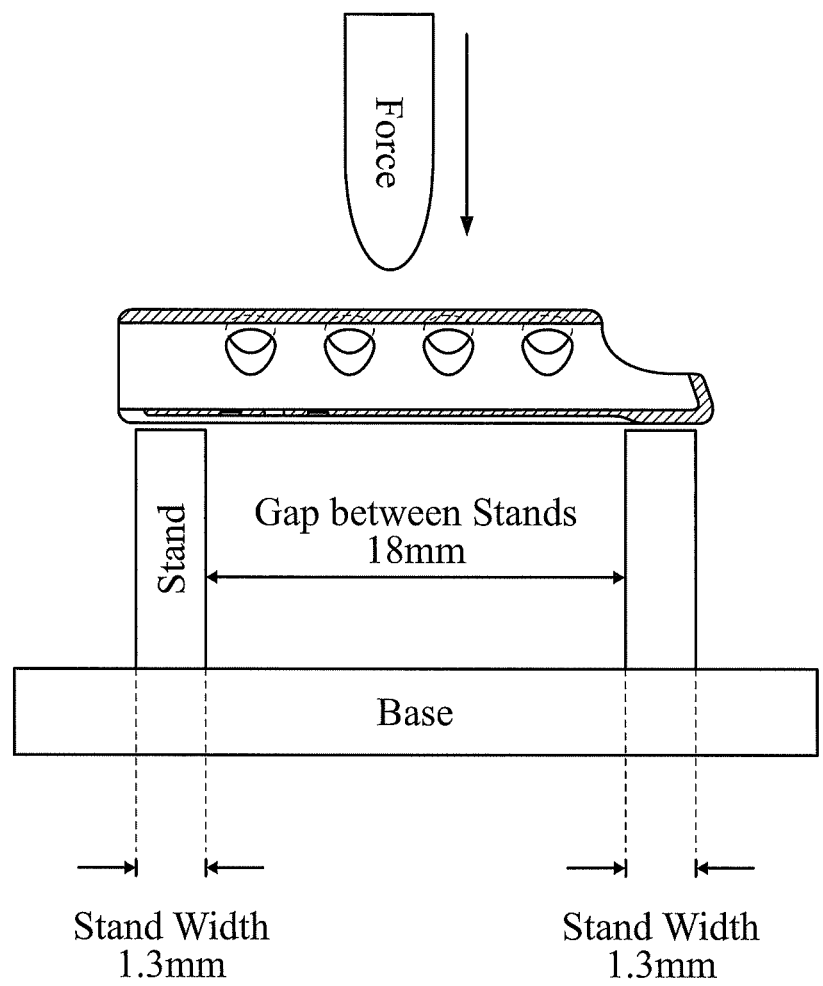
FIG. 5 is a depiction of the apparatus used in a three-point bend test of components according to the present invention.
Figure 6:
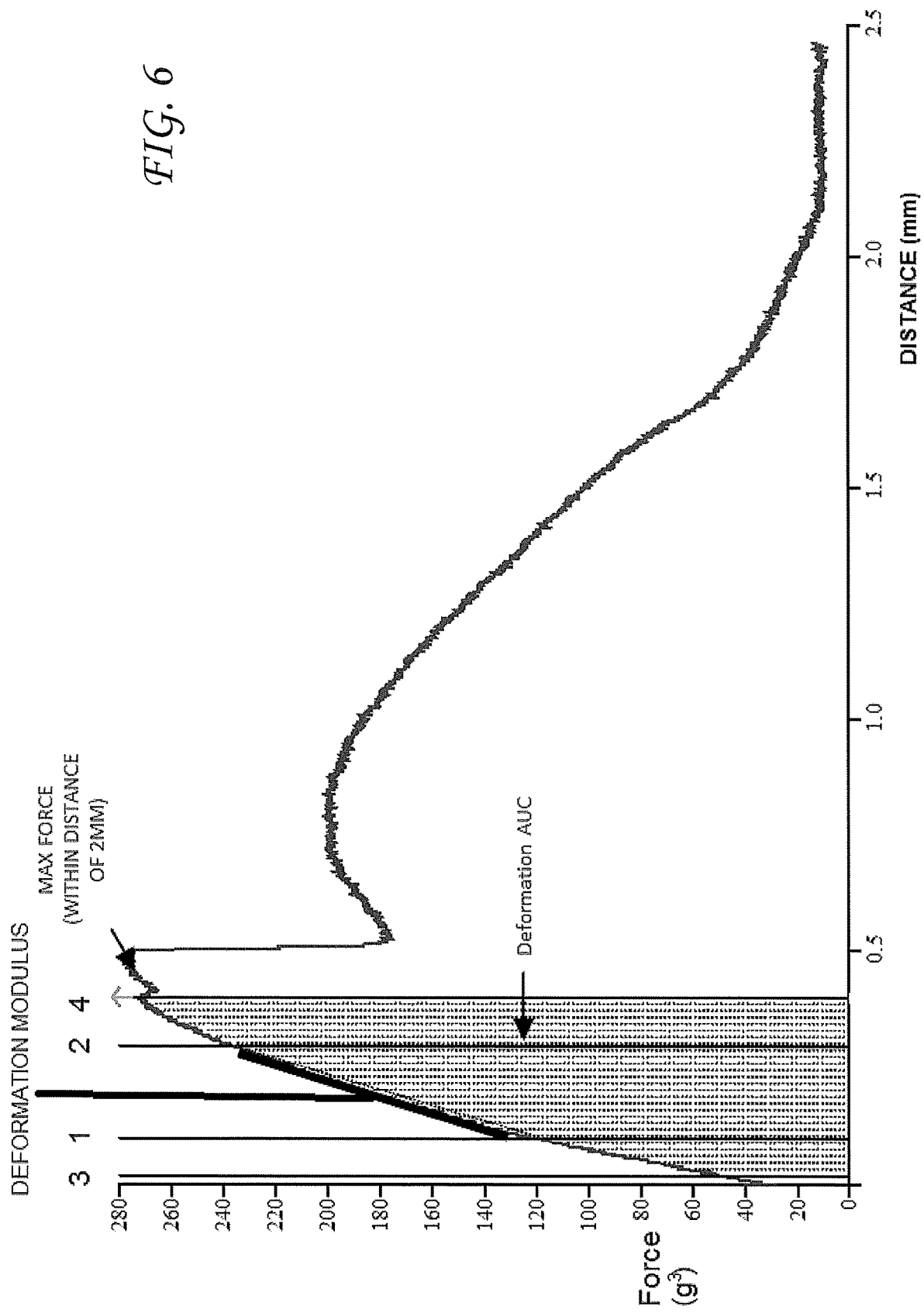
FIG. 6 shows the results of an assessment of the deformation modulus of a component according to the present disclosure following exposure to pH 2 conditions for 24 hours.
Figure 7:
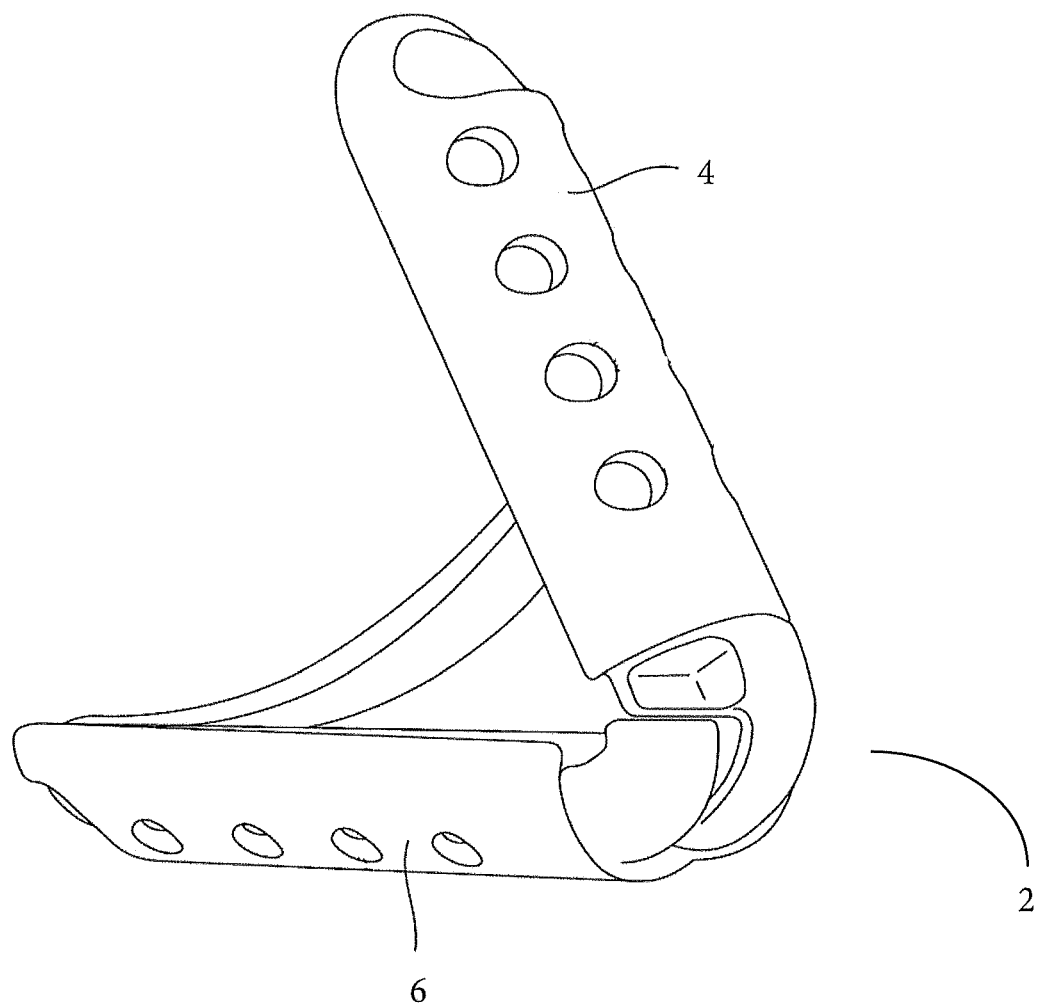
FIG. 7 depicts an exemplary embodiment of the present devices featuring a carrier portion, a first arm, and a second arm.

Test 2: Rigidity Under Upper Gastrointestinal Conditions—Rigidity [1] Test. In order to assess the ability of a device or component thereof to elude degradation and retain original stiffness under pH conditions associated with the upper gastrointestinal region (stomach and small intestine), the rigidity of a given component was measured both before and after exposure to low pH conditions. Each type A part was placed into a pharmacopoeia dissolution apparatus II, 400 mL, at 37° C., 100 RPM, containing HCl 0.1N+Xanthan 0.125 g/L (pH 2). Using a three-point bend test, the rigidity of each test component was measured after 1 hour, 4 hours, 8 hours, and 24 hours of exposure to the pH 2 test conditions. The three-point bend test was conducted by removing a given test component from the dissolution apparatus after the desired period of time, placing the test component into the three-point bend system adaptor of a TEXTUXE analyzer system (Stable Micro Systems Ltd., Godalming, Surrey, UK) having a load cell of 50 kg, a stand width of 1.3 mm, and a gap between stands of 18 mm. A depiction of the apparatus used in the 3-point bend test is provided in FIG. 5. The adaptor descended at a rate of 0.1 mm/sec. When a contact force of 5 grams is reached, the system begins recording the force of deformation, and such recording continued for 3 mm (30 seconds total). The deformation modulus (force/distance until maximum force), maximum force (obtained between 0 and up to 2 mm), and deformation AUC (F*distance) are recorded. A graph illustration of the results of one such test, using Sample 9 following exposure to pH 2 conditions for 24 hours, is shown in FIG. 6. Rigidity was defined as the maximum force recorded (between 0 and up to 2 mm) at the relevant time interval of the test. Percentage rigidity was calculated as follows:

% rigidity 1=((deformation force at 24 hours)/(deformation force at 1 hour))×100

The results for each component are shown in Table 9, below. Any component maintaining at least 60% of its original rigidity following 24 hours of exposure to test conditions is said to meet the requirement for rigidity.

TABLE 9 pH 2 phase - % rigidity1
(apparatus II, 400 CC 37°, 100 RPM
HCL 0.1N + Xanthan gum 0.125 g/L)
rigidity test = [deformation force at t = 1 hour]/
[deformation force at t = 24 hours]

| Composition Tested (Type A mold) | | rigidity at 1 hr (gr) | rigidity at 24 hr (gr) | % rigidity1 at 24 hr | Meets rigidity criteria? (% rigidity ≥60 at t = 24 hr) |
|---|---|---|---|---|---|
| Batch No. | Sample No. | | | | |
| A | 1 | 462.84 | 420.5 | 90.9 | Y |
| B | 2 | 240 | 152.4 | 63.5 | Y |
| B | 3 | 201.6 | 175.2 | 86.9 | Y |
| B | 4 | 148.4 | 120.1 | 80.9 | Y |
| C | 5 | 188.2 | 210.2 | 111.7 | Y |
| C | 6 | 209.7 | 247.5 | 118.0 | Y |
| C | 7 | 196.4 | 225.5 | 114.8 | Y |
| D | 8 | 253.9 | 86.7 | 34.1 | N |
| D | 9 | 245.1 | 273.1 | 111.4 | Y |
| D | 10 | 246.7 | 272.1 | 110.3 | Y |

Test 3: Degradability Under Post-Upper Gastrointestinal Conditions Rigidity [2] Test In order to assess the ability of a particular component to degrade in high pH conditions (as in the large intestine) to a degree necessary to ensure safe exit from the gastrointestinal tract, the rigidity of a given component was measured both before and after exposure to high pH conditions. Each type A component was placed into a pharmacopoeia dissolution apparatus II, 400 mL, at 37° C., 100 RPM, containing 6 g/L sodium phosphate (pH 6.8). Using a three-point bend test, the rigidity of each test component was measured after 2 hours, 4 hours, 8 hours, and 24 hours of exposure to the pH 6.8 test conditions. The three-point bend test was otherwise conducted as described above in connection with Test 2. Percentage rigidity was calculated as follows:

% rigidity 2=((deformation force at 24 hours pH 6.8)/(deformation force at 1 hour pH 2))×100

The results for each component are shown in Table 10, below. Any component retaining no more than 40% of its original rigidity following 24 hours of exposure to test conditions is said to meet the requirement for degradability.

TABLE 10 pH 6.8 phase - % rigidity2
(apparatus II, 400 mL, 37°, 100 RPM sodium phosphate 6/L, pH 6.8)
% rigidity2 = (rigidity at 24 hr pH 6.8)/(rigidity at t = 1 hr pH 2)*100

| Composition Tested (Type A mold) | | rigidity at 4 hr (gr) | rigidity at 8 hr (gr) | rigidity at 24 hr (gr) | % rigidity2 at 4 hr | % rigidity2 at 8 hr | % rigidity2 at 24 hr | Meets softness criteria? % rigidity ≤40% at 24 hr |
|---|---|---|---|---|---|---|---|---|
| Batch No. | Sample No. | | | | | | | |
| A | 1 | 410.5 | 404 | 405 | 88.7 | 87.3 | 87.5 | N |
| B | 2 | 16.8 | 0 | 0 | 7.0 | 0.0 | 0.0 | Y |
| B | 3 | 93.7 | 22.7 | 0 | 46.5 | 11.3 | 0.0 | Y |
| B | 4 | 31.3 | 0 | 0 | 21.1 | 0.0 | 0.0 | Y |
| C | 5 | 0 | 0 | 0 | 0.0 | 0.0 | 0.0 | Y |
| C | 6 | 187.4 | 127.7 | 25.5 | 89.4 | 60.9 | 12.2 | Y |
| C | 7 | 131.9 | 39.9 | 0 | 67.2 | 20.3 | 0.0 | Y |
| D | 8 | 0 | 0 | 0 | 0.0 | 0.0 | 0.0 | Y |
| D | 9 | 124.7 | 81.1 | 0 | 50.9 | 33.1 | 0.0 | Y |
| D | 10 | 94.2 | 11.9 | 0 | 38.2 | 4.8 | 0.0 | Y |

Throughout this application, various publications are referred to by first author and year of publication. Full citations for these publications are presented in a References section immediately before the claims. Disclosures of the publications cited in the References section are hereby incorporated by reference in their entireties into this application in order to more fully describe the state of the art as of the date of the invention described herein.

What is claimed is:

1. A gastric retentive device comprising a carrier portion comprising a first arm and a second arm and an active or diagnostic agent;
   wherein the active or diagnostic agent comprises part of at least one of the arms;
   wherein the at least one of the arms is configured to release the active or diagnostic agent into a subject's gastric environment following administration of the device thereto;
   wherein the carrier portion is coated with a polymer coating on its outer surface; and
   wherein when the device is in a collapsed configuration, the arms are in a closed configuration that is sized and shaped for oral administration; and
   wherein when the device is in an expanded configuration, the arms are shaped, sized, or both shaped and sized, such that the device does not pass through a pylorus; and
   wherein upon separation of at least one of the arms from the carrier portion, the device separates into two or more subparts that are individually sized or shaped to pass through the pylorus.

2. The device of claim 1, wherein the polymer coating comprises a polymethacrylate-based copolymer, a hydroxypropylmethylcellulose acetate succinate polymer, cellulose acetate, or a combination thereof.

3. The device of claim 1, wherein the polymer coating further comprises a plasticizer.

4. The device of claim 3, wherein the plasticizer is dibutyl sebacate, triacetin, triethyl citrate, acetyl tributyl citrate, acetyl triethyl citrate, polyethylene glycol, polyethylene glycol monomethyl ether, glycerin, sorbitol, sorbitan, castor oil, diacetylated monoglycerides, tributyl citrate, or a combination thereof.

5. The device of claim 3, wherein the plasticizer comprises between about 5 and about 26% of the weight of the polymer coating.

6. The device of claim 1, wherein the polymer coating thickness is from about 10 µm to about 200 µm.

7. The device of claim 1, wherein the percent weight gain of the device as a result of the polymer coating is from about 1% to about 10%.

8. The device of claim 1, wherein the arms are in the expanded configuration for at least six hours.

9. The device of claim 1, wherein the separation of at least one of the arms is configured to occur when at least 50% of the active or diagnostic agent has been released from the device into the gastric environment, upon exposure of the device to the gastric environment.

10. The device of claim 1, wherein the active or diagnostic agent is configured to release from the device over a time period of 3 to 24 hours, upon exposure of the device to the gastric environment.

11. The device of claim 1, wherein the drug or diagnostic agent is configured to release from the device over a time period of about 3 hours, about 6 hours, about 8 hours, about 10 hours, about 12 hours, about 14 hours, about 16 hours, about 18 hours, about 20 hours, about 22 hours, about 24 hours, about 28 hours, about 30 hours, about 32 hours, about 34 hours, about 36 hours, about 40 hours, about 44 hours, about 48 hours, about 60 hours, or about 72 hours.

12. The device of claim 1, wherein the active or diagnostic agent comprises an active pharmaceutical ingredient, or pharmaceutical salt thereof, selected from the list comprising prochlorperazine edisylate, ferrous sulfate, albuterol, aminocaproic acid, mecamylamine hydrochloride, procainamide hydrochloride, amphetamine sulfate, methamphetamine hydrochloride, benzphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, metformin, methylphenidate hydrochloride, theophylline cholinate, cephalexin hydrochloride, diphenidol, meclizine hydrochloride, prochlorperazine maleate, phenoxybenzamine, thiethylperazine maleate, anisindione, diphenadione erythrityl tetranitrate, digoxin, isoflurophate, acetazolamide, nifedipine, methazolamide, bendroflumethiazide, chlorpropamide, glipizide, glyburide, gliclazide, tobutamide, chlorproamide, tolazamide, acetohexamide, troglitazone, orlistat, bupropion, nefazodone, tolazamide, chlormadinone acetate, phenaglycodol, allopurinol, aluminum aspirin, methotrexate, acetyl sulfisoxazole, hydrocortisone, hydrocorticosterone acetate, cortisone acetate, dexamethasone, betamethasone, triamcinolone, methyltestosterone, 17-β-estradiol, ethinyl estradiol, ethinyl estradiol 3-methyl ether, prednisolone, 17-β-hydroxyprogesterone acetate, 19-norprogesterone, norgestrel, norethindrone, norethisterone, norethiederone, progesterone, norgesterone, norethynodrel, terfandine, fexofenadine, aspirin, acetaminophen, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, selegiline, chlorpromazine, methyldopa, dihydroxyphenylalanine, calcium gluconate, ketoprofen, ibuprofen, cephalexin, erythromycin, haloperidol, zomepirac, ferrous lactate, vincamine, phenoxybenzamine, diltiazem, milrinone, captropril, mandol, quanbenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinopril, enalapril, captopril, ramipril, enalaprilat, famotidine, nizatidine, sucralfate, etintidine, tetratolol, minoxidil, chlordiazepoxide, diazepam, amitriptyline, and imipramine, cyclosporins, cyclosporine A, insulin, coichicine, glucagon, thyroid stimulating hormone, parathyroid hormone, pituitary hormones, calcitonin, renin, prolactin, corticotrophin, thyrotropic hormone, follicle stimulating hormone, chorionic gonadotropin, gonadotropin releasing hormone, bovine somatotropin, porcine somatropin, oxytocin, vasopressin, prolactin, somatostatin, lypressin, pancreozymin, luteinizing hormone, LHRH, interferons, interleukins, growth hormones such as human growth hormone, bovine growth hormone and porcine growth hormone, fertility inhibitors such as the prostaglandins, fertility promoters, growth factors, or human pancreas hormone releasing factor.

13. The device of claim 1, wherein the expanded configuration resists passage through the pylorus prior to release of at least 40%, at least 50%, at least 70%, at least 80%, at least 90%, or at least 95% of the drug or diagnostic agent from the device.

14. The device of claim 1, wherein the device comprises multiple subparts.

15. The device of claim 1, wherein the device comprises more than 5 subparts.

16. The device of claim 1, wherein the device separates into more than 5 subparts.

17. A method of delivering an active or diagnostic agent to a subject's gastric environment for at least about 3 hours comprising orally administering the gastric retentive device of claim 1 to the subject.

18. The method of claim 17, wherein the active or diagnostic agent is delivered to the subject's stomach for about 3 hours, about 6 hours, about 8 hours, about 10 hours, about 12 hours, about 14 hours, about 16 hours, about 18 hours, about 20 hours, about 22 hours, about 24 hours, about 28 hours, about 30 hours, about 32 hours, about 34 hours, about 36 hours, about 40 hours, about 44 hours, about 48 hours, about 60 hours, or about 72 hours.

19. The method of claim 17, wherein the administration is once daily, twice daily, or several times daily.

20. The method of claim 17, wherein the administration frequency is once every 2 days to once every 14 days.

* * * * *